US012600949B2

(12) United States Patent
Su et al.

(10) Patent No.: US 12,600,949 B2
(45) Date of Patent: Apr. 14, 2026

(54) MODIFIED MACROPHAGES, COMPOSITIONS AND USES THEREOF

(71) Applicant: DUOGENIC STEMCELLS CORPORATION, Taichung City (TW)

(72) Inventors: Hong-Lin Su, Taichung City (TW); Ching-I Shen, Kaohsiung City (TW); Fu-Hui Wang, Taichung City (TW); Chia-Ying Hsieh, Taichung City (TW); Masataka Kiyokawa, Kyoto (JP)

(73) Assignee: DUOGENIC STEMCELLS CORPORATION, Taichung City (TW)

( * ) Notice: Subject to any disclaimer, the term of this patent is extended or adjusted under 35 U.S.C. 154(b) by 712 days.

(21) Appl. No.: 17/919,564

(22) PCT Filed: Apr. 19, 2021

(86) PCT No.: PCT/JP2021/015925
§ 371 (c)(1),
(2) Date: Oct. 18, 2022

(87) PCT Pub. No.: WO2021/215410
PCT Pub. Date: Oct. 28, 2021

(65) Prior Publication Data
US 2023/0142987 A1 May 11, 2023

(30) Foreign Application Priority Data
Apr. 20, 2020 (AU) ................................. 2020901243

(51) Int. Cl.
| C12N 5/0786 | (2010.01) |
| A61K 40/17 | (2025.01) |
| A61K 40/22 | (2025.01) |
| A61K 40/24 | (2025.01) |
| A61K 40/41 | (2025.01) |

(52) U.S. Cl.
CPC ............ *C12N 5/0645* (2013.01); *A61K 40/17* (2025.01); *A61K 40/22* (2025.01); *A61K 40/24* (2025.01); *A61K 40/416* (2025.01); *A61K 2239/31* (2023.05); *A61K 2239/38* (2023.05); *C12N 2501/15* (2013.01); *C12N 2501/22* (2013.01); *C12N 2501/2304* (2013.01); *C12N 2501/231* (2013.01); *C12N 2501/2313* (2013.01); *C12N 2502/115* (2013.01); *C12N 2533/52* (2013.01)

(58) Field of Classification Search
None
See application file for complete search history.

(56) References Cited

U.S. PATENT DOCUMENTS

| 2007/0253938 A1 | 11/2007 | Ciombor et al. |
| 2017/0112971 A1 | 4/2017 | Spiller |
| 2019/0134090 A1 | 5/2019 | Hematti et al. |

FOREIGN PATENT DOCUMENTS

| JP | 2017136014 A | * | 8/2017 |
| WO | 0233050 A2 | | 4/2002 |
| WO | 2008007941 A1 | | 1/2008 |
| WO | 2013181746 A1 | | 12/2013 |
| WO | 2014106666 A1 | | 7/2014 |
| WO | 2019108756 A1 | | 6/2019 |
| WO | 2020006385 A2 | | 1/2020 |

OTHER PUBLICATIONS

Sesia, Sergio B., et al. "Anti-Inflammatory/tissue repair macrophages enhance the cartilage-forming capacity of human bone marrow-derived mesenchymal stromal cells." Journal of cellular physiology 230.6 (2015): 1258-1269. (Year: 2016).*
Dai, Meilu, et al. "Cartilage repair in degenerative osteoarthritis mediated by squid type II collagen via immunomodulating activation of M2 macrophages, inhibiting apoptosis and hypertrophy of chondrocytes." Biomaterials 180 (2018): 91-103. (Year: 2018).*
Shen, Hua, et al. "The effect of mesenchymal stromal cell sheets on the inflammatory stage of flexor tendon healing." Stem Cell Research & Therapy 7 (2016): 1-13. (Year: 2016).*
Hu, Yue, et al. "Quercetin alleviates rat osteoarthritis by inhibiting inflammation and apoptosis of chondrocytes, modulating synovial macrophages polarization to M2 macrophages." Free Radical Biology and Medicine 145 (2019): 146-160. (Year: 2019).*
Zhang, Yin, et al. "Development and prospect of intra-articular injection in the treatment of osteoarthritis: a review." Journal of Pain Research (2020): 1941-1955. (Year: 2020).*
Hu, Jian Ming, et al. "CD163 as a marker of M2 macrophage, contribute to predict aggressiveness and prognosis of Kazakh esophageal squamous cell carcinoma." Oncotarget 8.13 (2017): 21526. (Year: 2017).*
International-type search for Australia provisional patent application No. 2020901243, mailed Jun. 16, 2020.
Sergio B. Sesia et al., "Anti-Inflammatory/Tissue Repair Macrophages Enhance the Cartilage-Forming Capacity of Human Bone Marrow-Derived Mesenchymal Stromal Cells," Journal of Cellular Physiology, Jun. 2015, pp. 1258-1269, vol. 230, No. 6.
L. Utomo et al., "Cartilage inflammation and degeneration is enhanced by pro-inflammatory (M1) macrophages in vitro, but not inhibited directly by anti-inflammatory (M2) macrophages," Osteoarthritis and Cartilage, Jul. 2016, pp. 2,162-2,170, vol. 24, No. 12.

(Continued)

*Primary Examiner* — Tracy Vivlemore
*Assistant Examiner* — Fatimah Khalaf Matalkah
(74) *Attorney, Agent, or Firm* — Pilloff Passino & Cosenza LLP; Rachel K. Pilloff; Sean A. Passino

(57) ABSTRACT

The present invention provides modified monocytes, modified macrophages, pharmaceutical compositions comprising the modified monocytes or modified macrophages described herein and at least one pharmaceutically acceptable carrier or excipient. Uses of the modified monocytes or the modified macrophages for the treatment of musculoskeletal diseases and inducing cartilage formation are provided. Also disclosed herein are in vitro culture methods for generating the modified macrophages.

17 Claims, 22 Drawing Sheets

(56)                    References Cited

OTHER PUBLICATIONS

Atanas Todorov et al., "Monocytes Seeded on Engineered Hypertrophic Cartilage Do Not Enhance Endochondral Ossification Capacity," Tissue Engineering: Part A., Jul. 2017, pp. 708-715, vol. 23, No. 13-14.

Caroline Neu et al., "CD14-Dependent Monocyte Isolation Enhances Phagocytosis of Listeria monocytogenes by Proinflammatory. GM-CSP-Derived Macrophages," PLOS One, Jun. 2013. Vol. 8., Issue 6. e66898.

Nicolai A. Kittan et al., "Cytokine Induced Phenotypic and Epigenetic Signatures Are Key to Establishing Specific Macrophage Phenotypes," PLOS One, Oct. 2013. Vol. 8, Issue 10. e78045.

Gerardo García-González et al., "Triggering of protease-activated receptors (PARs) induces alternative M2 macrophage polarization with impaired plasticity," Molecular Immunology, Aug. 2019, pp. 278-288, vol. 114.

R F Schelbergen et al., "Alarmins SIO0A8 and SIO0A9 Stimulate Production of Pro-inflammatory Cytokines in M2 Macrophages without Changing Their M2 Membrane Phenotype," Ann Rheum Dis, Feb. 2012. vol. 71. Suppl 1: A76.

Audrey Paoletti et al., "Increased MicroRNA-155 Is Associated with a Specific Defect of Antiinflammatory M2 Macrophages Polarization Both in Human Rheumatoid Arthritis and in Collagen-Induced-Arthritis Mice," Ann Rheum Dis, May 2019, pp. 1092-1093, vol. 78, Suppl 2.

International Search Report and Written Opinion for PCT/JP2021/015925, mailed Jul. 6, 2021.

Office Action for related Taiwan application 110113873, mailed Jul. 7, 2022.

Second Office action in Taiwan application No. 110113873, mailed Nov. 11, 2022.

Third Office action in Russia application No. 2022127443, mailed Mar. 23, 2025.

Third Office action in Taiwan application No. 110113873, mailed Mar. 22, 2024.

Francisco J. Rios et al., "Isolation and Differentiation of Human Macrophages," Methods in Molecular Biology, Jan. 2017, pp. 311-320, vol. 1527. doi: 10.1007/978-1-4939-6625-7_24.

Extended European Search Report in Europe application No. 21791825. 9, mailed May 16, 2024.

Jean-Michel Dayer et al., "Collagens Act as Ligands to Stimulate Human Monocytes to Produce Mononuclear Cell Factor (MCF) and Prostaglandins (PGE2)," Collagen and Related Research, Nov. 1982, pp. 523-540, vol. 2, No. 6. doi: 10.1016/s0174-173x(82)80007-1.

Heidi S. Schultz et al., "OSCAR-collagen signaling in monocytes plays a proinflammatory role and may contribute to the pathogenesis of rheumatoid arthritis," European Journal of Immunology, Feb. 9, 2016, pp. 952-963, vol. 46, No. 4. doi: 10.1002/eji.201545986.

First Office action in Japan application No. 2022-551557, mailed Mar. 27, 2024.

First Office action in Korea application No. 10-2022-7036229, mailed May 29, 2024.

Samuele Tardito et al., "Macrophage M1/M2 polarization and rheumatoid arthritis: A systematic Review," Autoimmunity Reviews, Sep. 11, 2019, pp. 1-21, vol. 18(11), 102397. doi: 10.1016/j.autrev.2019.102397.

Second Office action in Russia application No. 2022127443, mailed Dec. 23, 2024.

Ans T Van Der Ploeg et al., "Pompe's disease," The Lancet, Oct. 11, 2008, pp. 1,342-1,353, vol. 372 (9646). doi: 10.1016/S0140-6736(08)61555-X.

Laura A.G. Armas et al., "Pathophysiology of Osteoporosis New Mechanistic Insights," Endocrinol Metab Clin N Am, Sep. 2012, pp. 475-486, vol. 41(3). doi: 10.1016/j.ecl.2012.04.006. Epub Jun. 9, 2012.

ЯРИЛИН А. А., ИммуНоЛогИЯ: у4 бН иК ГЭ ОТАР-Ме ди. 2010, 749 с., с. 166, а бЗа Ц4.

Cekurova N. R., et al., The Effect of Cryoprotectants On Electric Parameters of Mouse Embryo Cell Membranes, the Effect of Cryoprotectants On Electric Param., 0253-7673, 1990, No. 1, pp. 30-33 (abstract translated).

Second Office action in Saudi Arabia application No. 522440958, mailed Jun. 9, 2024.

First Office action in Vietnam application No. 1-2022-06719, mailed Jan. 23, 2025.

Stephen Chiu et al., "Role of monocytes and macrophages in regulating immune response following lung transplantation," Curr Opin Organ Transplant, Jun. 2016, pp. 239-245, vol. 21, No. 3.

Office action in Vietnam application No. 1-2022-06719, mailed Oct. 17, 2025.

* cited by examiner

[Fig. 1]
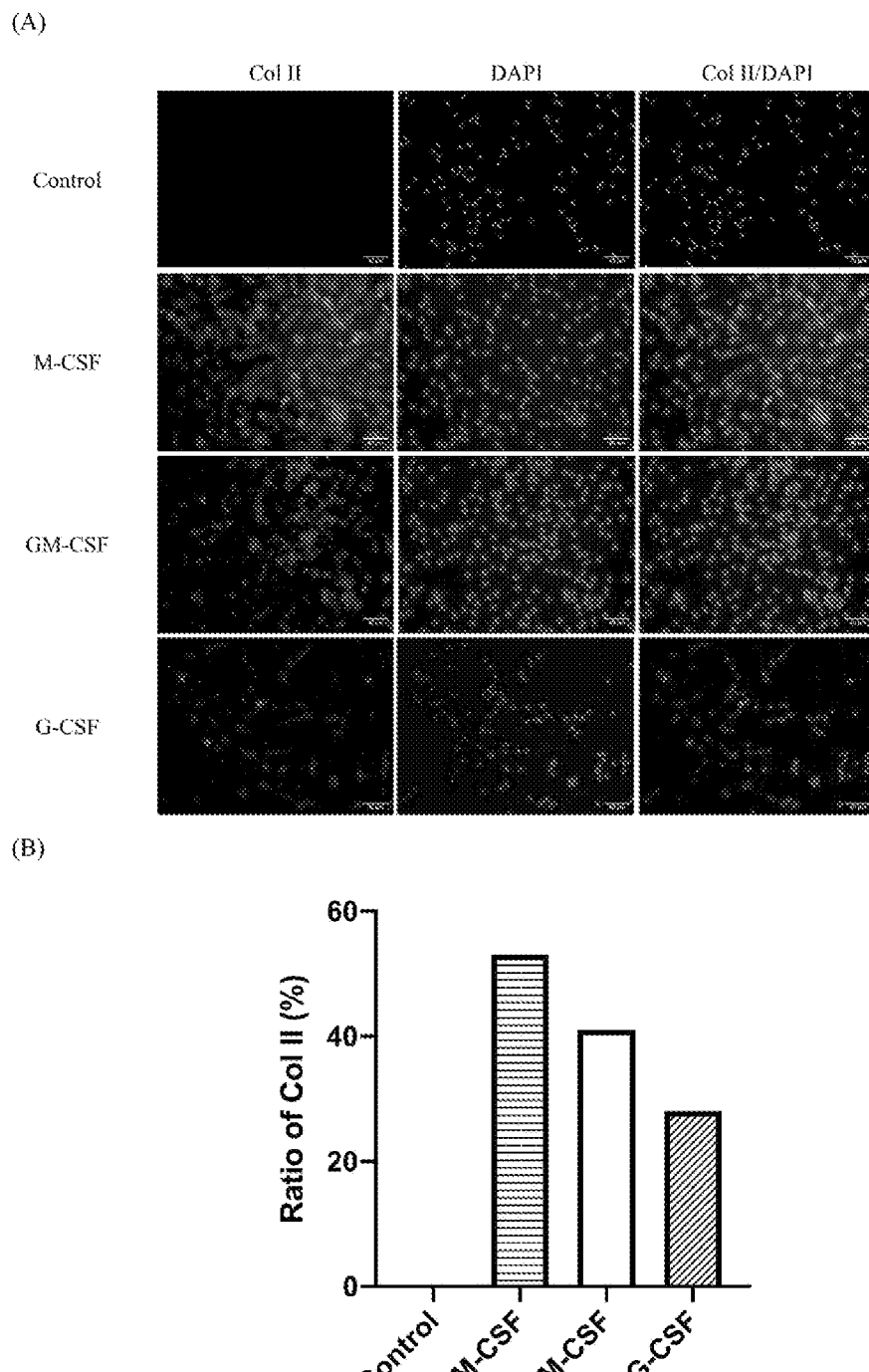

[Fig. 2]
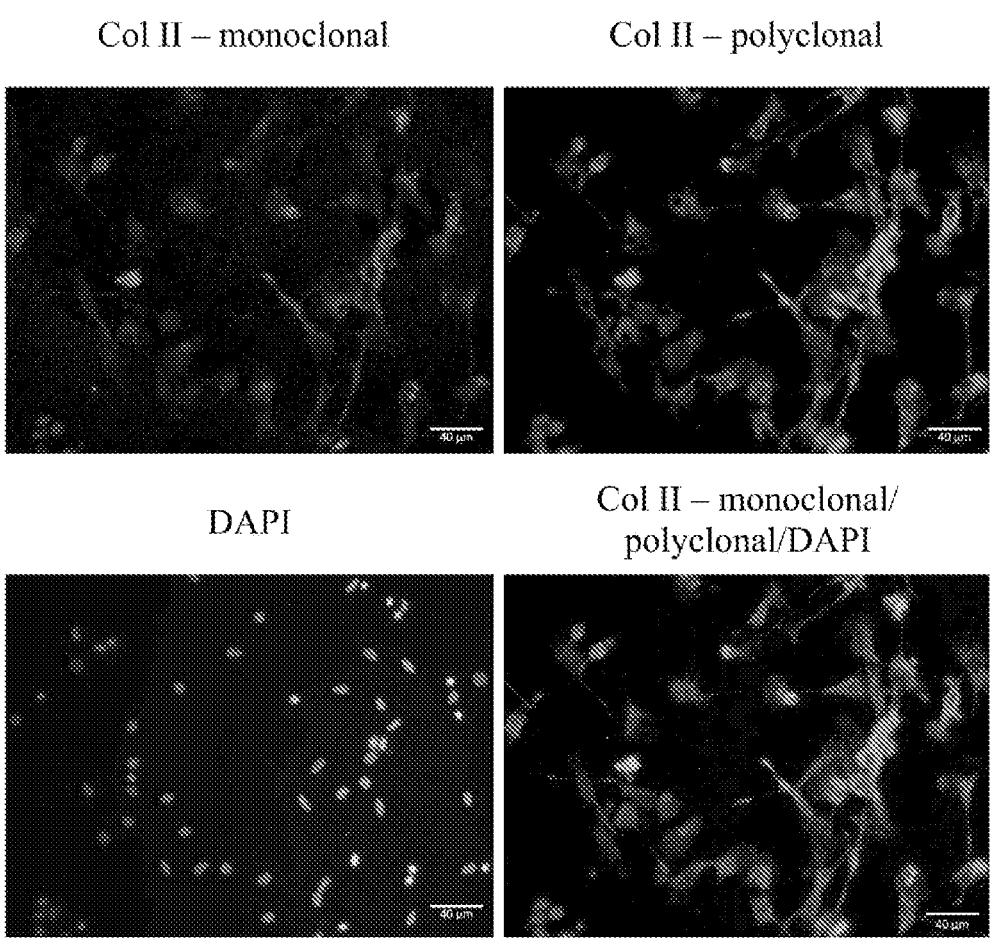
[Fig. 3A]
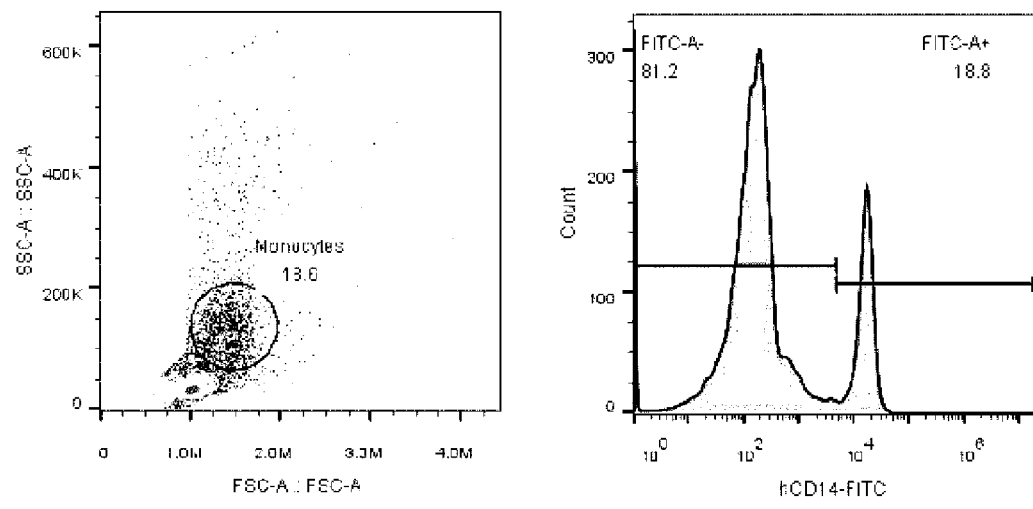

[Fig. 3B]
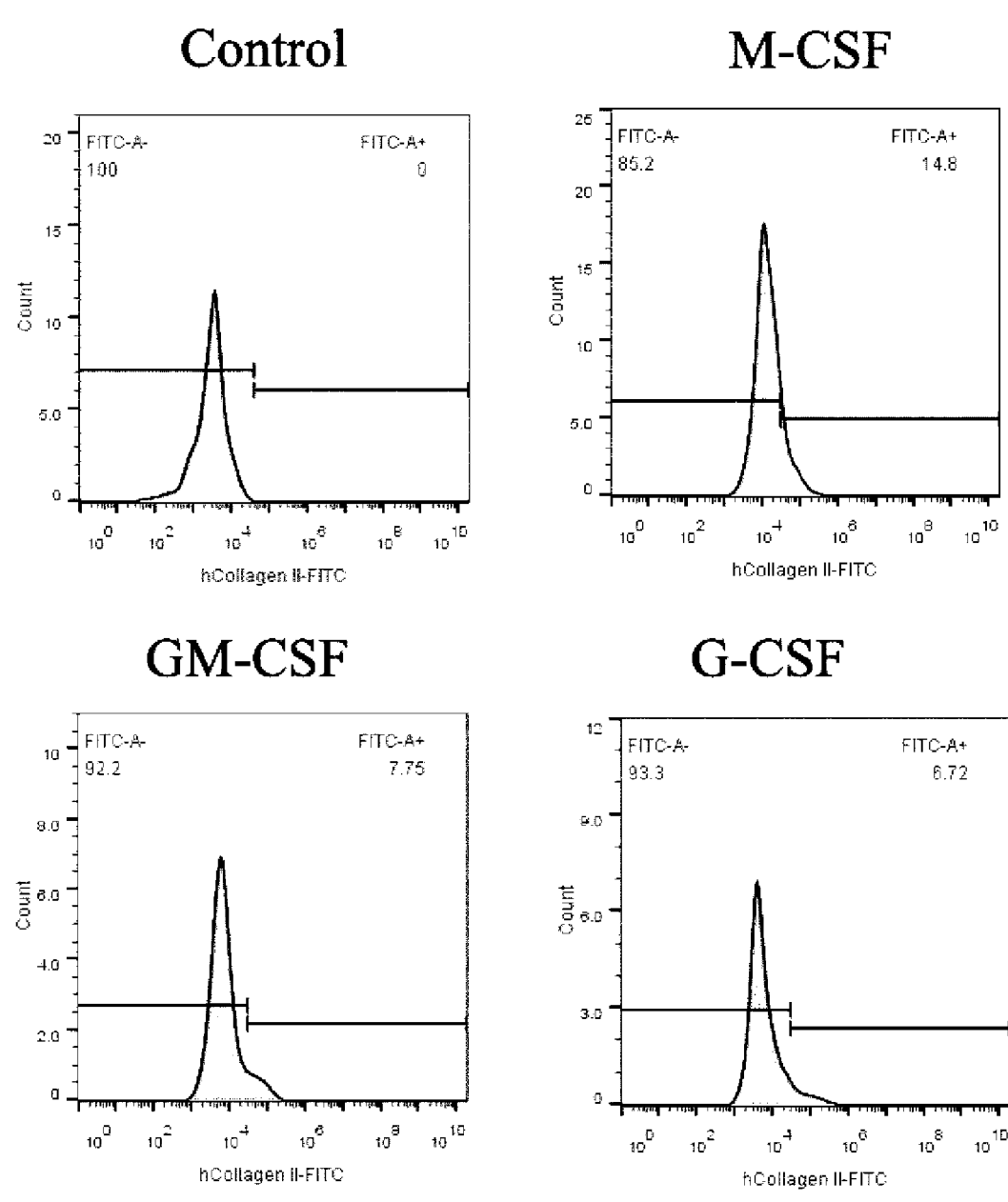

[Fig. 3C]
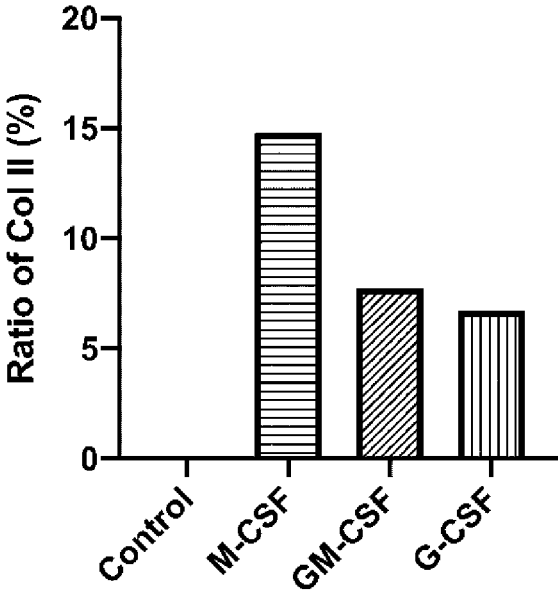
[Fig. 4A]
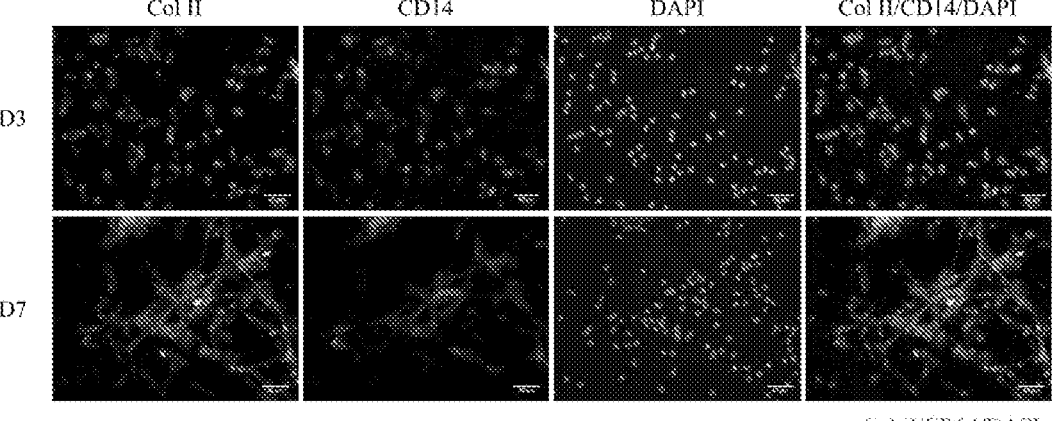

[Fig. 4B]
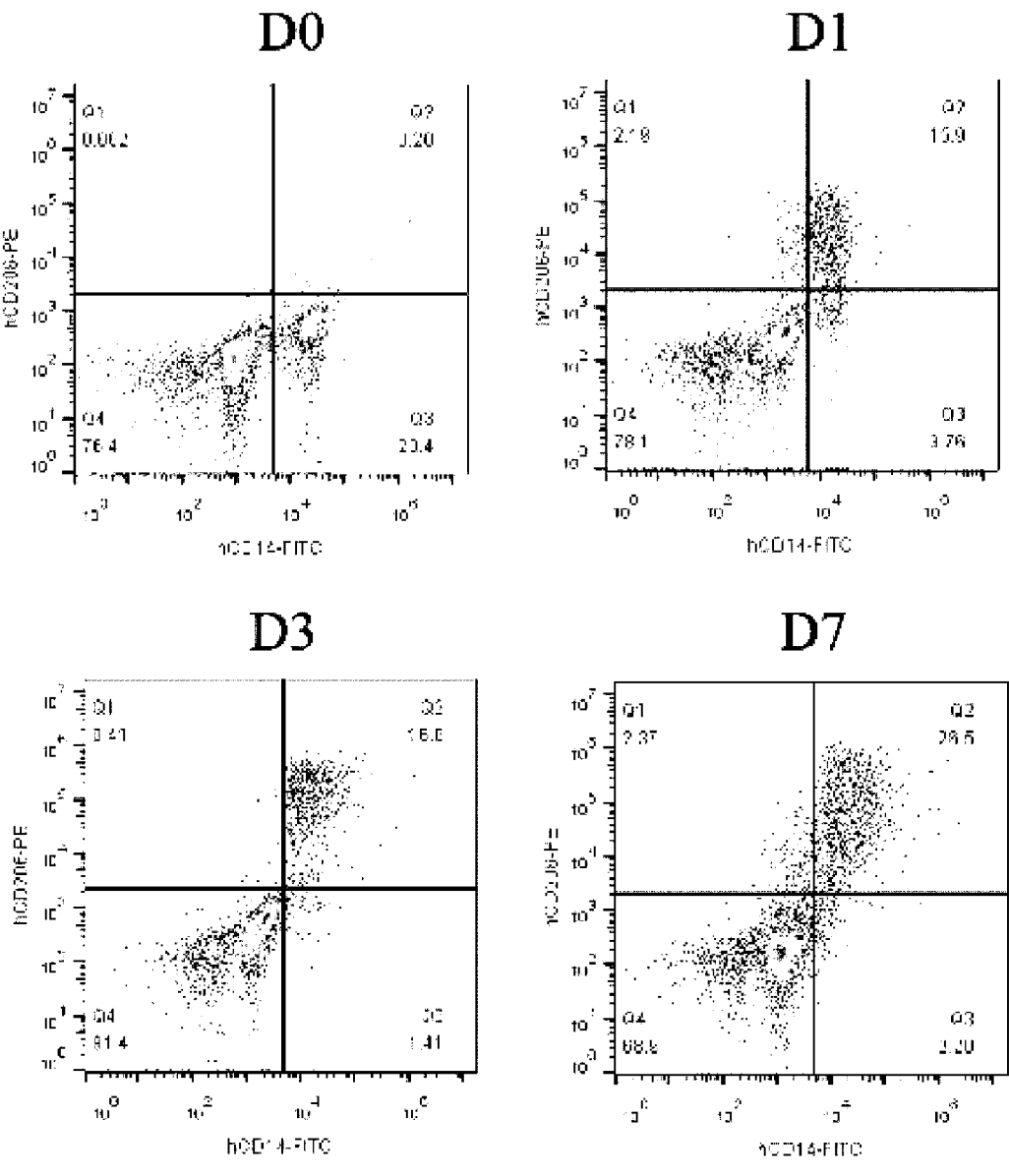

[Fig. 4C]
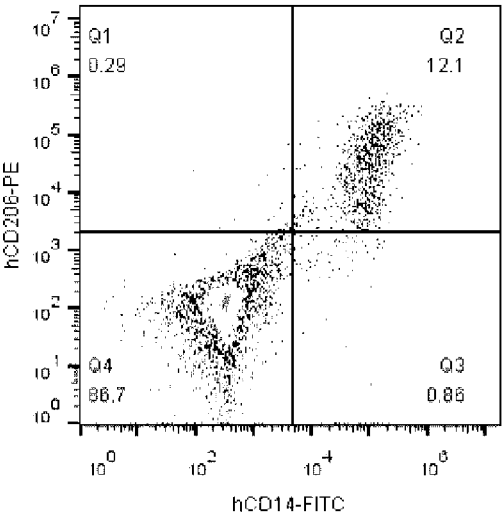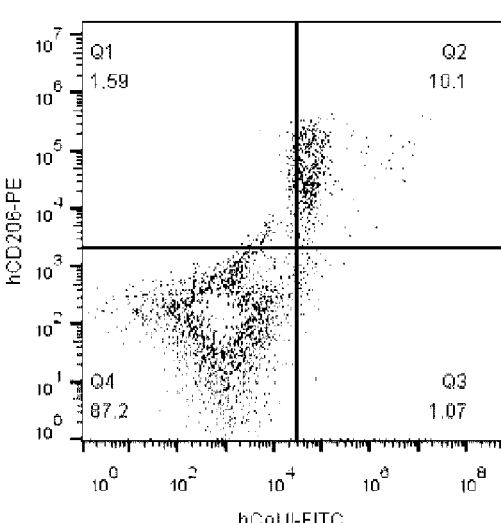

[Fig. 5]
(A)
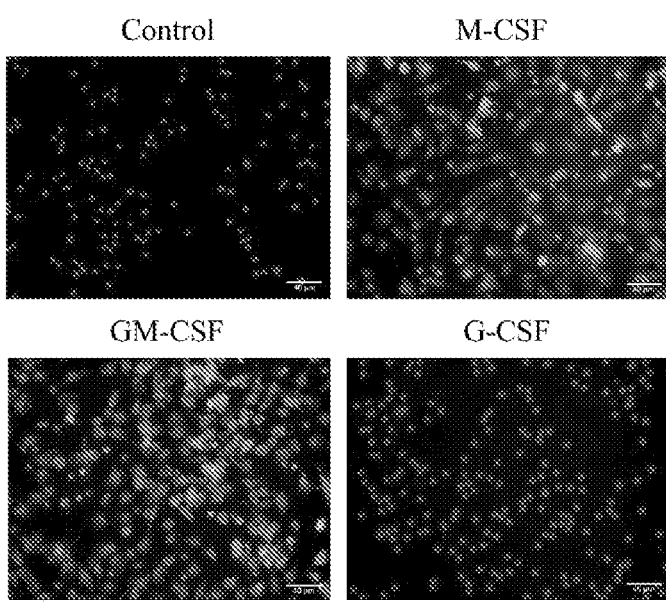
Col II/CD206/DAPI
(B)
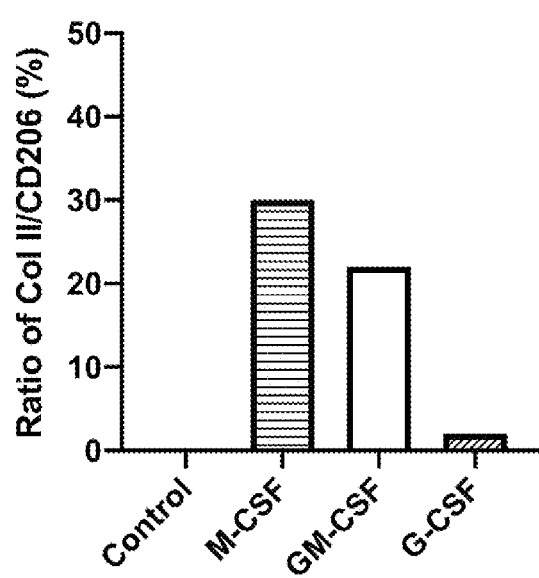

[Fig. 6A]
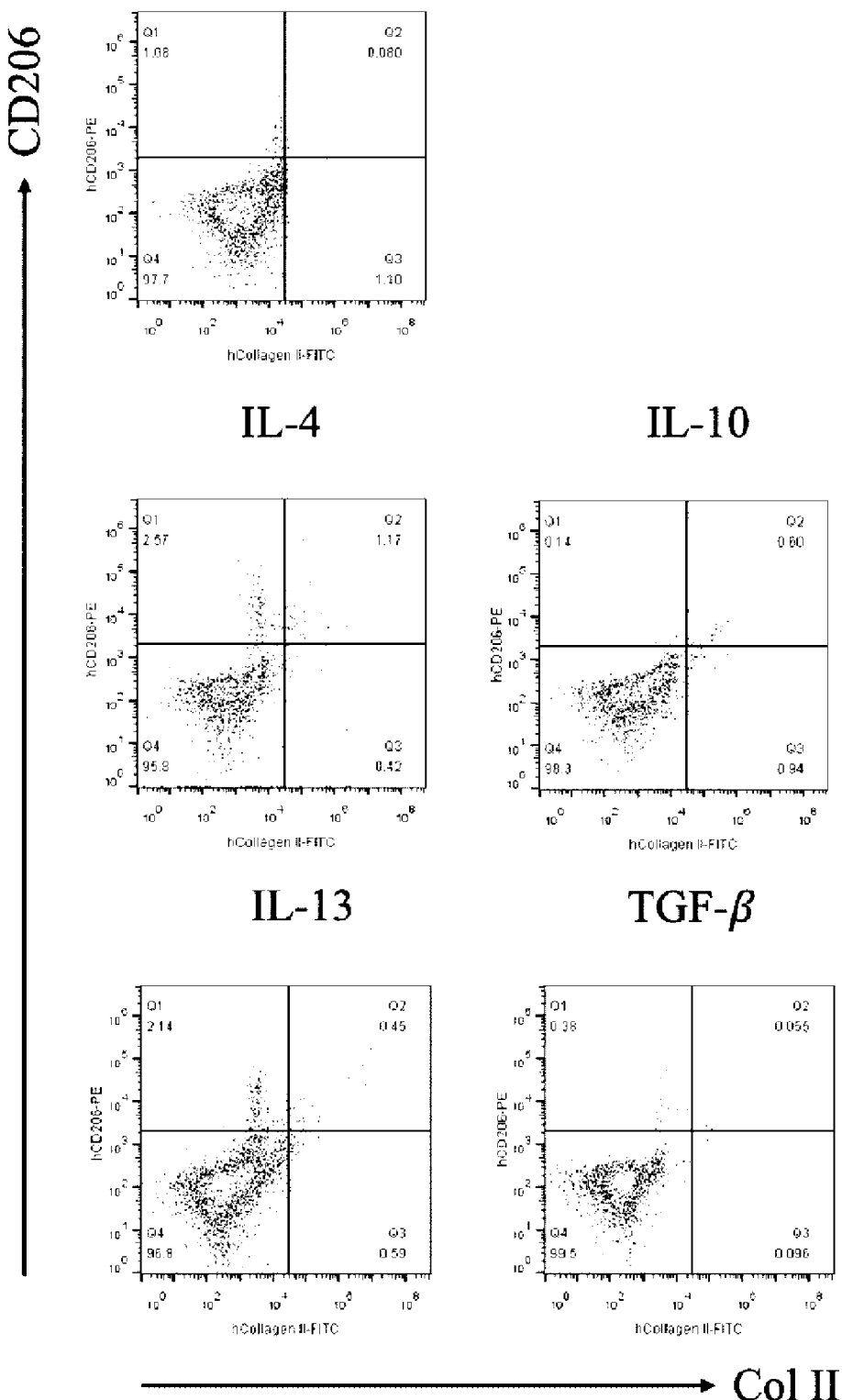

[Fig. 6B]
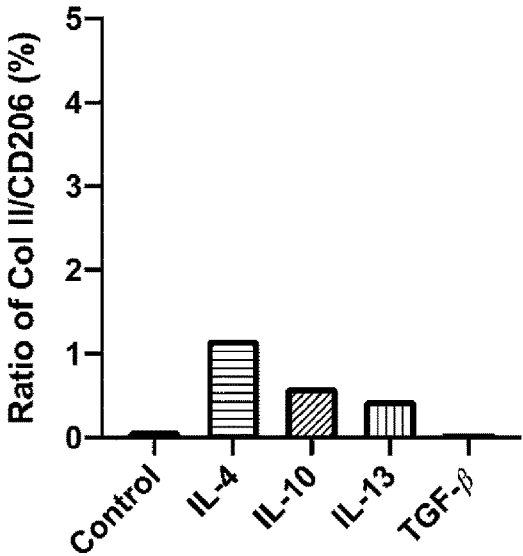
[Fig. 7A]
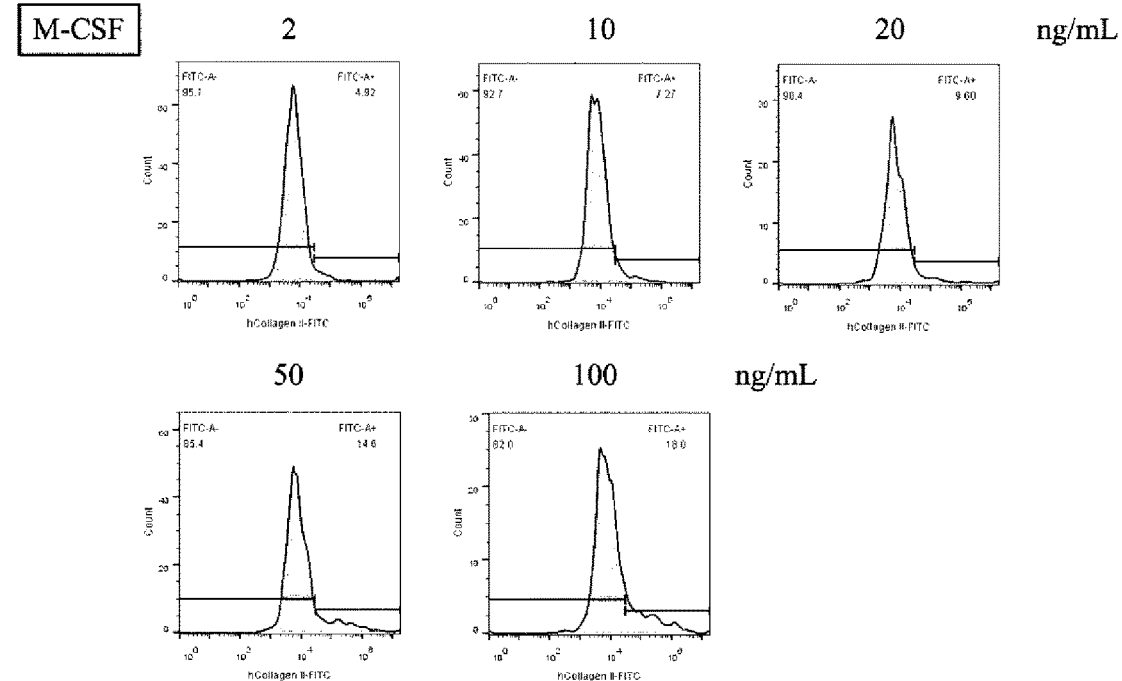

[Fig. 7B]
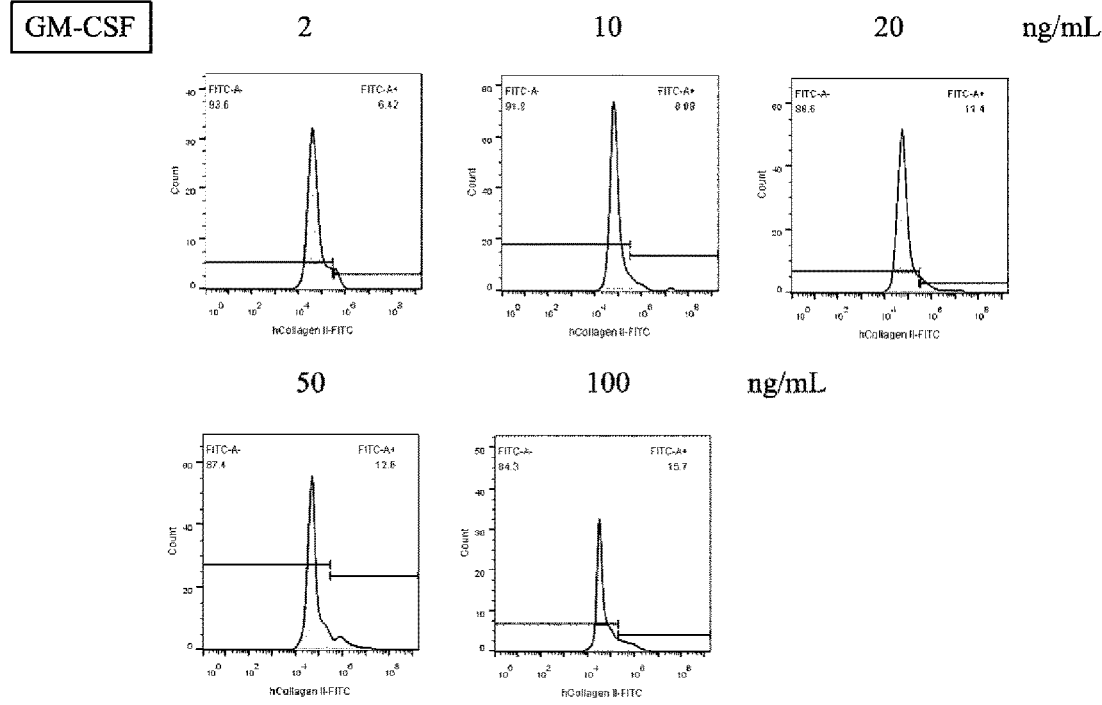
[Fig. 7C]
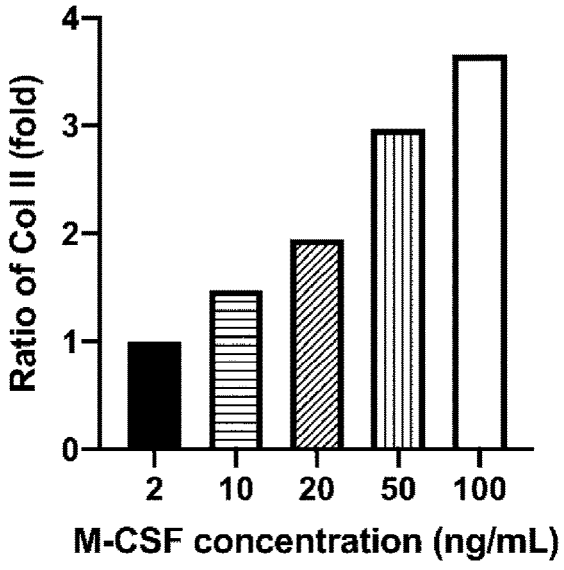

[Fig. 7D]
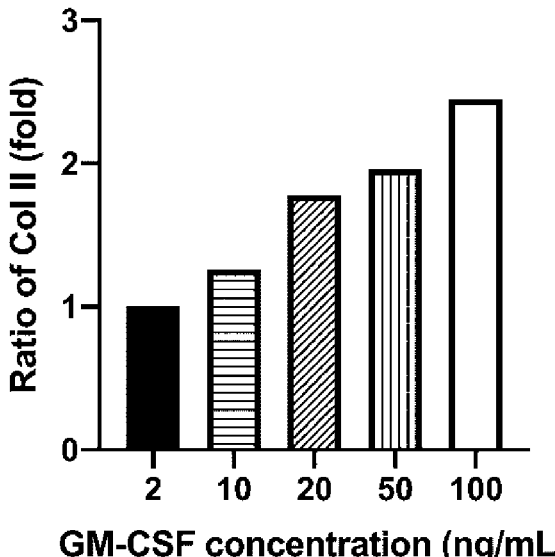

[Fig. 8]
(A)
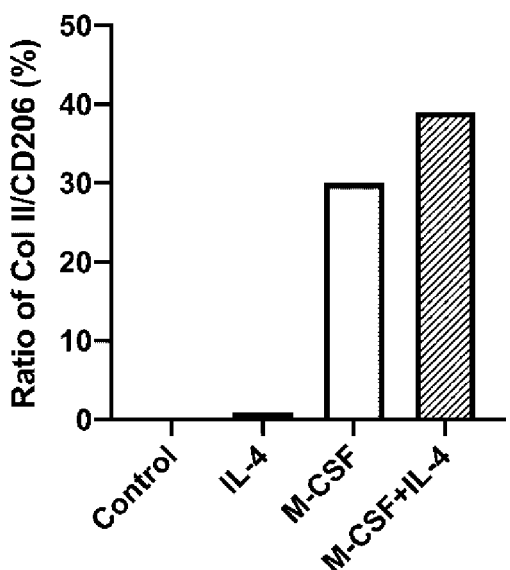
(B)
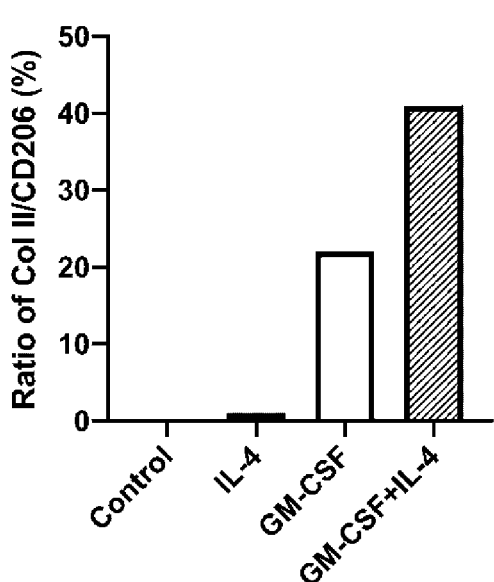

[Fig. 9A]
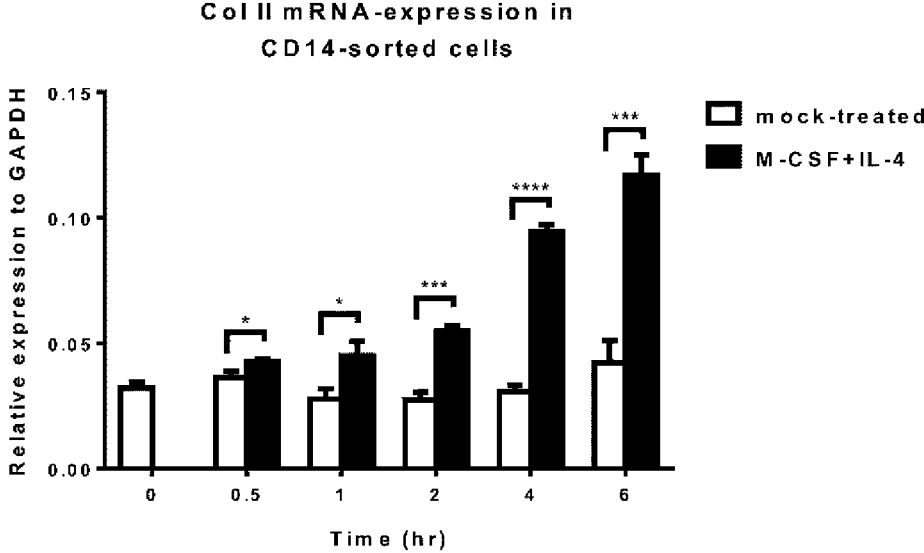
[Fig. 9B]
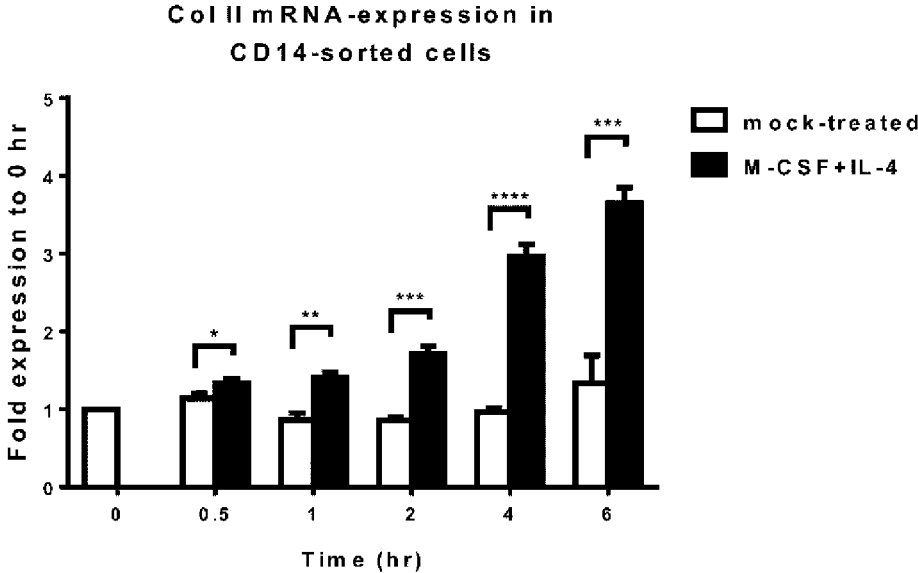

[Fig. 9C]
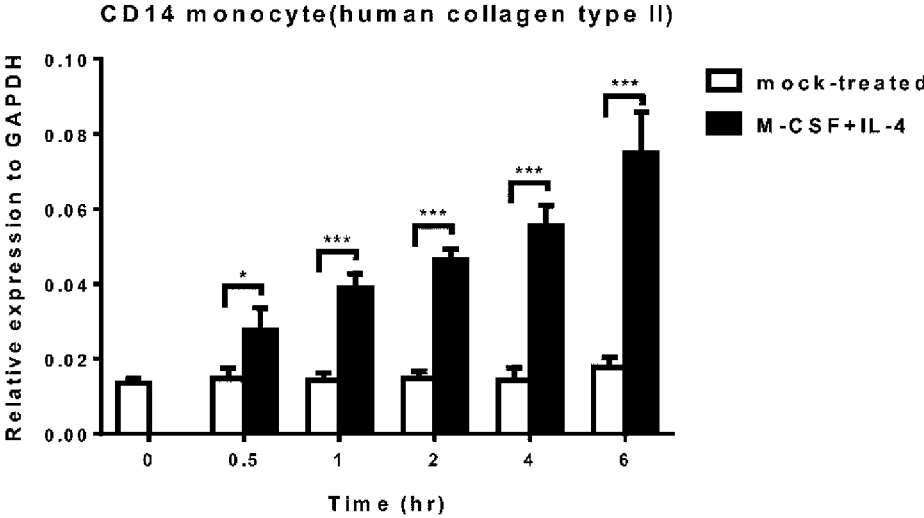
[Fig. 9D]
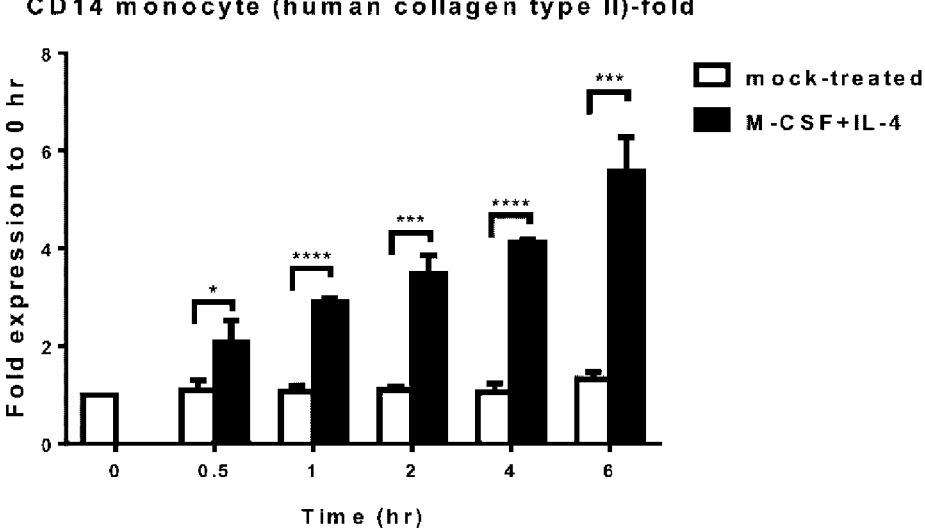

[Fig. 10A]
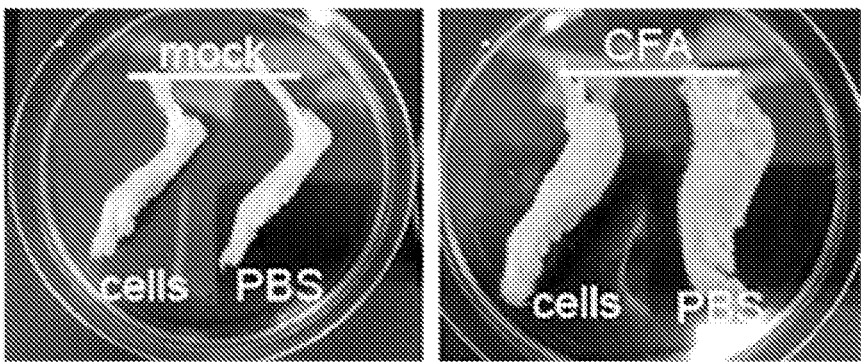
[Fig. 10B]
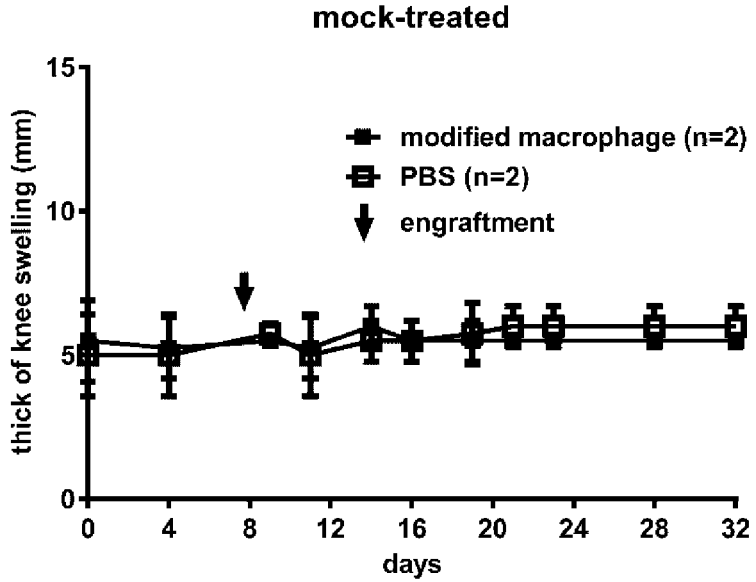

[Fig. 10C]
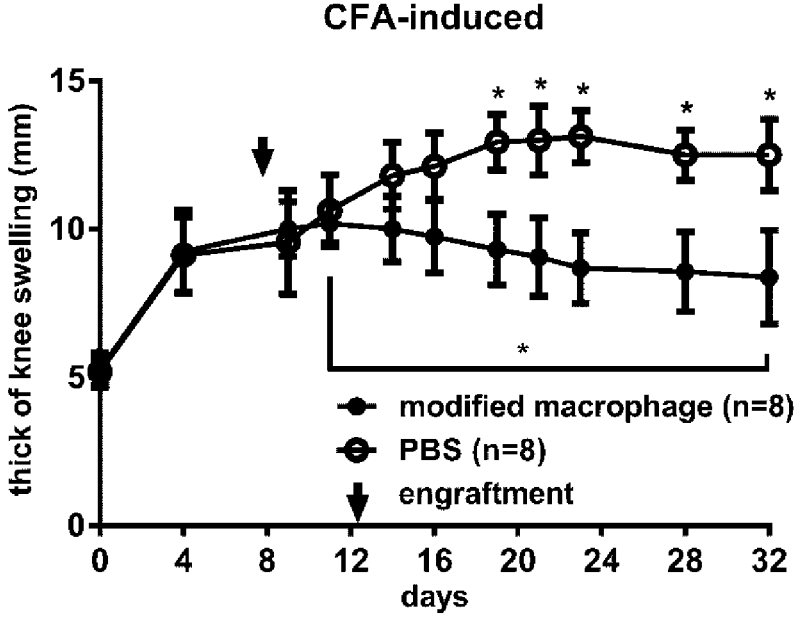
[Fig. 11]
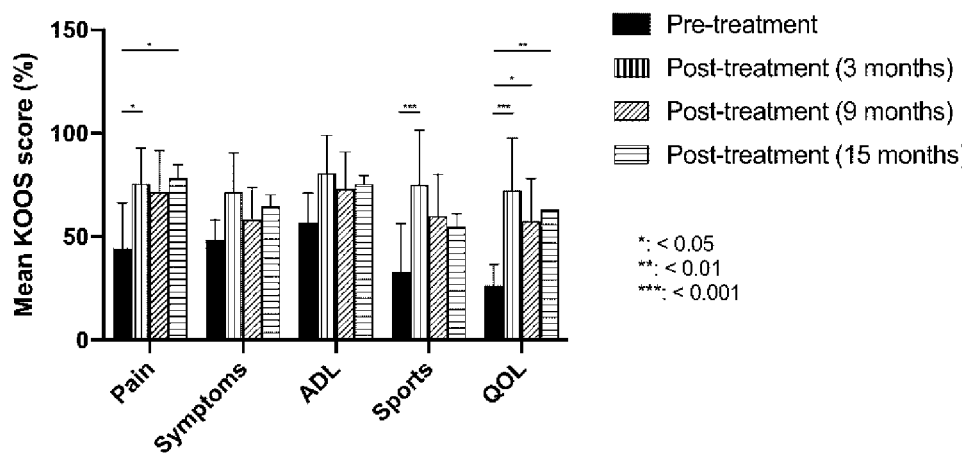

[Fig. 12A]
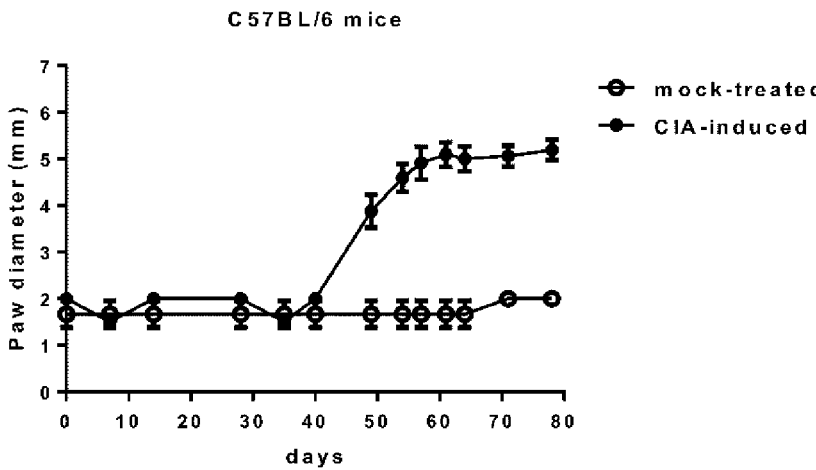
[Fig. 12B]
(B)
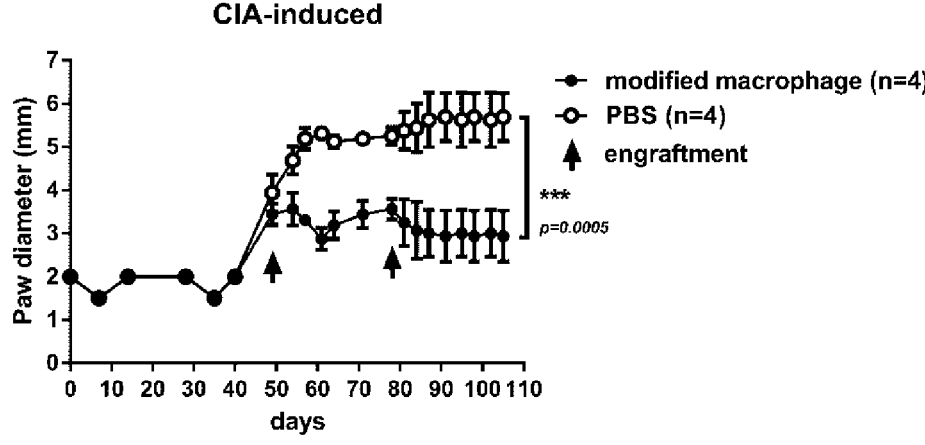

[Fig. 12C]
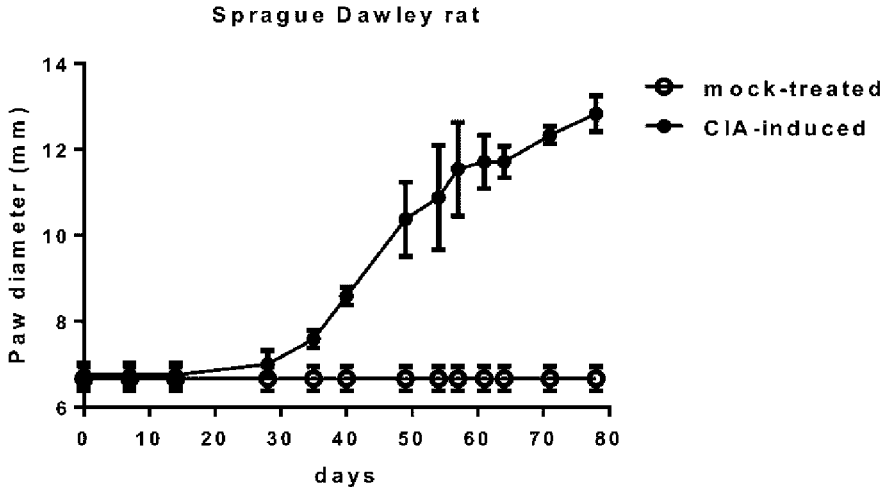
[Fig. 12D]
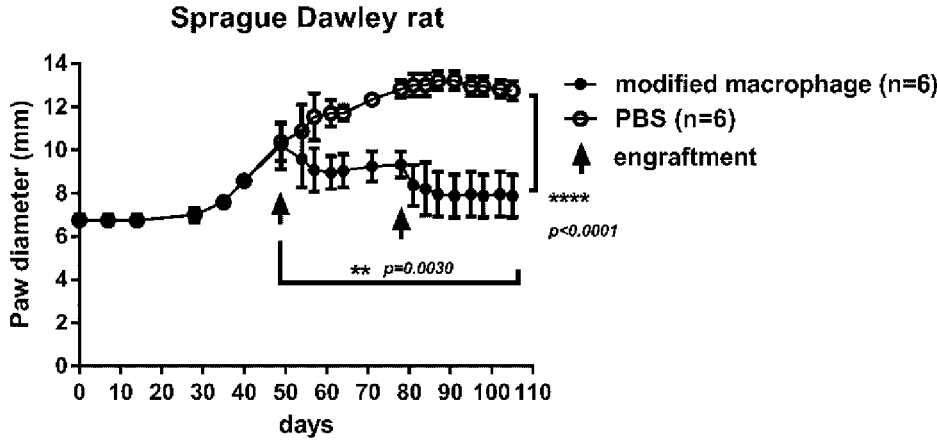

[Fig. 13]
Pre-treatment       Post-treatment
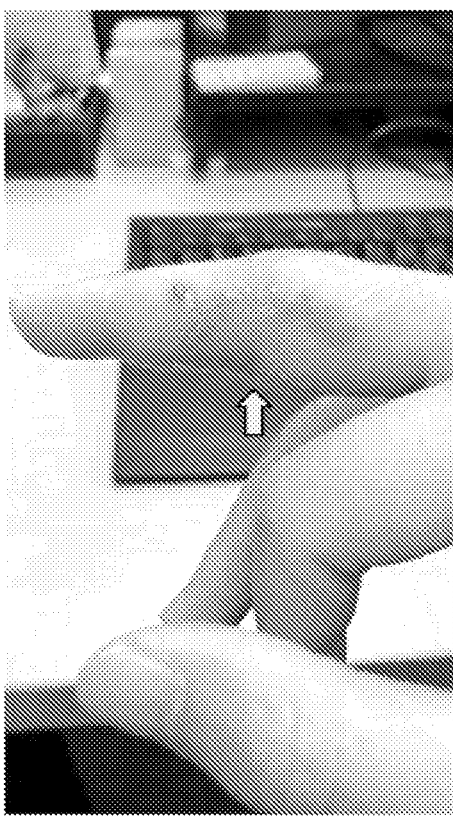 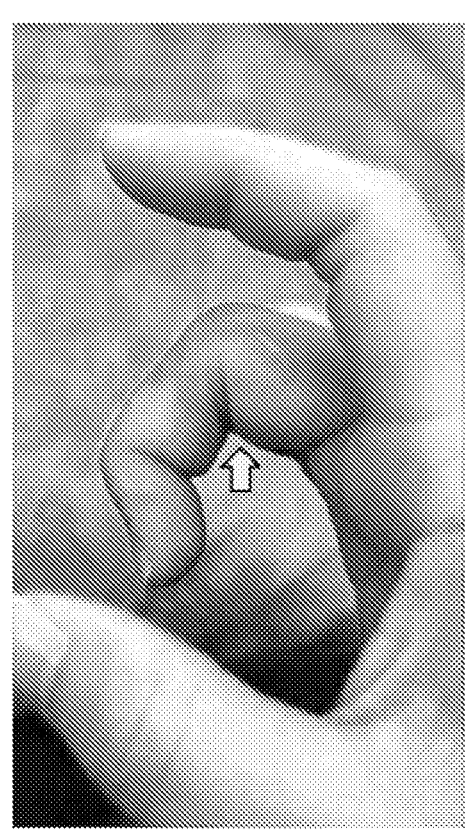

[Fig. 14]
(A)
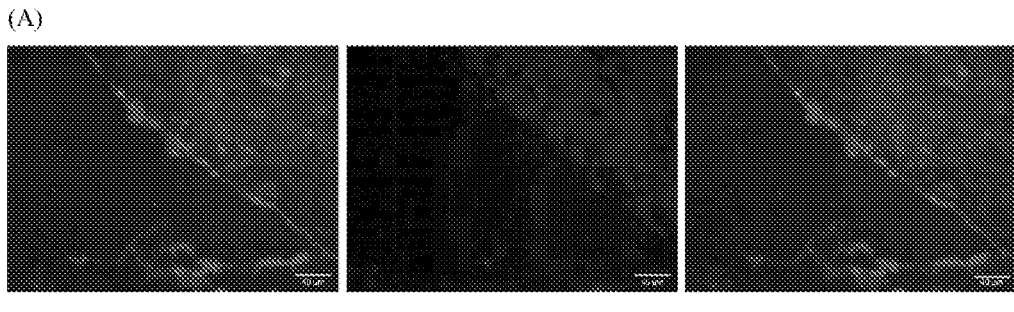
Col II, DAPI
(B)
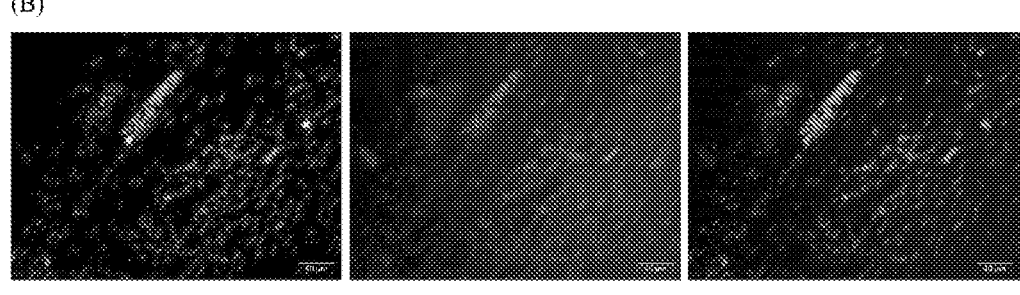
Col II, DAPI
(C)
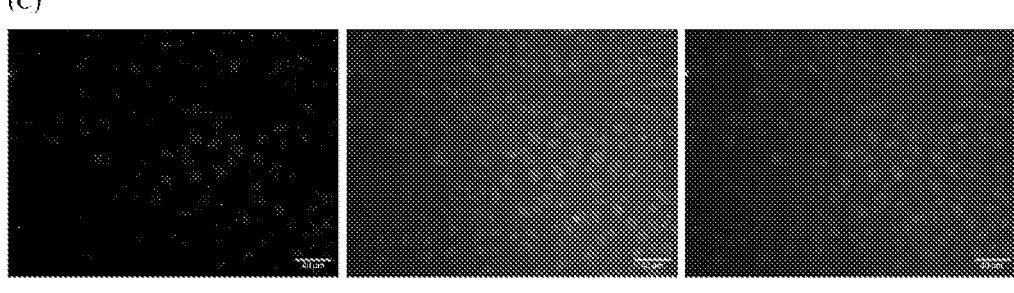
Col II, DAPI

[Fig. 15A]
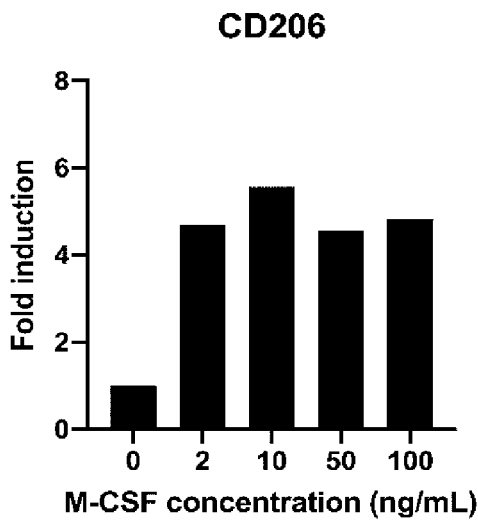
[Fig. 15B]
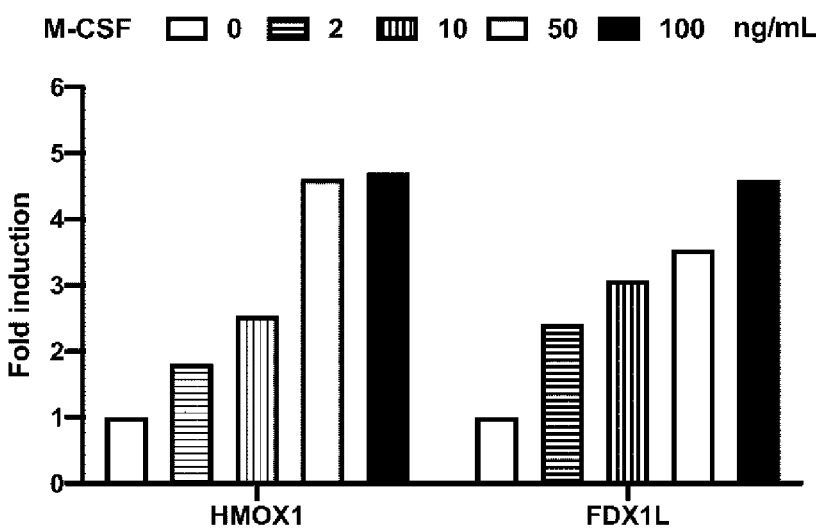

[Fig. 15C]
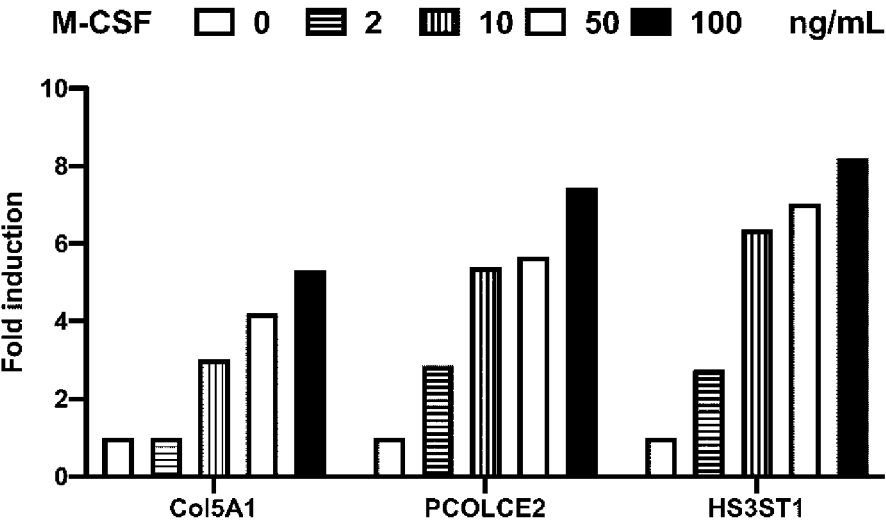

MODIFIED MACROPHAGES, COMPOSITIONS AND USES THEREOF

CROSS-REFERENCES TO RELATED APPLICATION

This application claims the benefit of priority from Australian Provisional Application No. 2020901243, filed 20 Apr. 2020, the entire content of which is incorporated herein by reference.

TECHNICAL FIELD

The invention relates to modified macrophages, pharmaceutical compositions comprising the same and uses thereof. Also provided are methods for generating modified macrophages disclosed herein.

BACKGROUND ART

Osteoarthritis (OA) represents the most common musculoskeletal disease. More than 50 million Americans are affected by OA in 2020 and it is predicted to increase to 70 million within the next twenty years as a result of aging population and an increase in life expectancy, making it the fourth leading cause of disability. OA is characterized by progressive degeneration of the articular cartilage with synovial inflammation (synovitis) and neovascular invasion into the articular surface. Severe OA is accompanied by progressively subchondral bone destruction, osteophyte formation, bone marrow remodeling and meniscal lesions.

Accumulative evidence suggests macrophages play a crucial role in the development of OA. In the normal synovium, macrophages are the primary immune cells and the front-line responder to joint injury. Macrophages in the OA synovium, however, cause cartilage destruction by producing matrix metalloproteinases and inflammatory cytokines, such as IL-1$\beta$ and TNF-$\alpha$. Increased number of macrophages in OA synovium is correlated with the degree of synovial angiogenesis and synovitis. A recent study by van der Heijden et al. shows that the numbers of activated macrophages are positively associated with the OA severity and the disease progression using noninvasive imaging with a folate receptor-$\beta$-based agent.

Although depletion of macrophages in animal models of OA markedly reduced osteophyte formation, such depletion also leads to enhanced synovial inflammation. This result may be caused by two functionally distinct subtypes of macrophages, M1 and M2. M1 macrophages are pro-inflammatory and can be polarized by granulocyte macrophage-colony stimulating factor (GM-CSF). In contrast, M2 macrophages are anti-inflammatory and can be polarized by macrophage colony-stimulating factor (M-CSF) to reduce synovitis. These results suggest the optimal polarization approach is critical for the role of the macrophage in the management of OA.

The human collagen matrix, such as type II collagen (Col II), is a crucial and nonrenewable component of the adult joint cartilage. Col II stimulates the secretion of cartilage glycosaminoglycans (GAGs) by chondrocytes and enhances cartilage repair in animal models. However, Col II shows very limited turnover during the life span of an adult with or without OA.

Current OA therapies include pain relief with oral NSAIDs or selective cyclooxygenase 2 (COX-2) inhibitors, intra-articular (IA) injection with agents such as corticosteroids and hyaluronan and surgical approaches. Although hyaluronan is used to lubricate damaged-joint, this treatment does not regenerate hyaline cartilage or modify disease progression. Despite advances in understanding the biology of OA and other musculoskeletal diseases and the availability of new treatment options to treat musculoskeletal disorders, promoting the healing of damaged or defective tendon/joint is needed.

The present invention provides a population of modified macrophages expressing Col II to satisfy these and other needs. The modified macrophages can be used in autologous therapy or in non-autologous therapy.

SUMMARY OF THE INVENTION

In one embodiment, the present invention provides one or more phenotypically distinct and modified macrophages, comprising a macrophage, carrying a phenotype of CD14 and CD206 (i.e., CD14$^+$CD206$^+$) and expressing type II collagen (Col II).

In another embodiment, the present invention provides one or more phenotypically distinct and modified monocytes, comprising a monocyte, carrying a phenotype of CD14 (i.e., CD14) and expressing type II collagen (Col II).

Some embodiments provide pharmaceutical compositions comprising a modified macrophage or modified monocyte described herein and a pharmaceutically acceptable carrier or excipient.

Other embodiments provide methods of treating a musculoskeletal disease, comprising administering an effective amount of the modified macrophages or modified monocytes described herein to a subject in need thereof, wherein the symptoms and signs of musculoskeletal disease are reduced.

Also provided are methods for inducing cartilage formation in a body site of a subject, comprising the step of administering the modified macrophage or modified monocytes disclosed herein to the body site of the subject in need thereof.

The modified macrophage described herein can be produced in vitro by contacting at least one monocyte with a composition comprising (a) a cell culture medium and (b) a polarization mixture. The modified macrophages cultured or polarized by methods of the present invention possess the characteristic phenotype of M2 macrophages (i.e., CD14$^+$ CD206$^+$) and expresses Col II.

The culturing methods described herein allow for generating modified macrophages from a fixed amount of a sample (for example, 10 ml of peripheral blood mononuclear cells, PBMNCs).

The terms "invention," "the invention," "this invention" and "the present invention" used in this patent are intended to refer broadly to all of the subject matter of this patent and the patent claims below. Statements containing these terms should be understood not to limit the subject matter described herein or to limit the meaning or scope of the patent claims below. Embodiments of the invention covered by this patent are defined by the claims below, not this summary. This summary is a high-level overview of various aspects of the invention and introduces some of the concepts that are further described in the Detailed Description section below. This summary is not intended to identify key or essential features of the claimed subject matter, nor is it intended to be used in isolation to determine the scope of the claimed subject matter. The subject matter should be understood by reference to appropriate portions of the entire specification, any or all drawings and each claim.

The invention will become more apparent when read with the accompanying figures and detailed description which follow.

BRIEF DESCRIPTION OF DRAWINGS

Illustrative embodiments of the present invention are described in detail below with reference to the following Figures:

FIG. 1, panel A is an assembly of fluorescent immuno-cytochemistry staining images of Col II expressed in the PBMNCs cultured in different types of polarization mixture on day 3. The cultured PBMNCs were stained and Col II expressed in the cytoplasm and on cytoplasmic membrane as green. The nuclei were stained with DAPI as blue. Panel B is a bar graph illustrating the % of collagen expressed in the cultured PBMNCs cultured in different types of polarization mixture.

FIG. 2 is an assembly of fluorescent immunocytochem-istry staining images of Col II expressed in the cytosol and on cytoplasmic membrane of the cultured PBMNCs, con-firmed by specific monoclonal and polyclonal antibodies against human Col II. The nuclei were stained with DAPI as blue.

FIG. 3 is an assembly of images of flow cytometric analysis of the FSC/SSC spectrum and CD14-FITC histo-gram (panel A) of the cultured PBMNCs, showing that the gated population correlated to the CD14$^+$ monocyte popu-lation. The expression of Col II (panel B) of PBMNCs cultured in different types of polarization mixture was analyzed on day 3. Panel C illustrates the % of Col II expressed in the gated CD14$^+$ monocytes, derived from PBMNCs cultured in different types of polarization mixture.

FIG. 4, panel A is an assembly of fluorescent immuno-cytochemistry staining images of Col II (green) expression in CD14$^+$ monocytes (red), derived from M-CSF treated PBMNCs on day 3 and day 7. Panel B illustrates the expression profile of CD206 in CD14$^+$ monocytes cells, derived from PBMNCs cultured in M-CSF from day 0 to day 7. Panel C illustrates the co-expression of CD206 and Col II in CD14$^+$ monocytes cells on Day 5 (i.e., phenotype of modified macrophages). The presence of CD206 indicates the cultured CD14$^+$ monocytes have matured into modified macrophages.

FIG. 5, panel A is an assembly of fluorescent immuno-cytochemistry staining images of Col II (red) and CD206 (green) expression in PBMNCs cultured in different types of polarization mixture. Panel B illustrates the ratio of co-expression of Col II/CD206 (i.e., phenotype of modified macrophages) in PBMNCs cultured in different types of polarization mixture.

FIG. 6, panel A is an assembly of flow cytometry images and panel B is a bar graph illustrating the effect of various cytokines on the expression of Col II and CD206 of modified macrophages cultured in different types of polarization mixture.

FIG. 7 is an assembly of flow cytometric analysis images showing the dose-effect of M-CSF (panel A) and GM-CSF (Panel B) on Col II expression in modified macrophages on day 3. Panels C and D are bar graphs showing the dose-effect of M-CSF (panel C) and GM-CSF (Panel D) on Col II expression in modified macrophages.

FIG. 8 includes bar graphs illustrating the ratio of Col II/CD206 modified macrophages of cultured PBMNCs with IL-4 and/or M-CSF (Panel A) and IL-4 and/or GM-CSF (Panel B), based on the results of the immunocytochemical staining on day 3.

FIG. 9, panel A is a bar graph showing Col II mRNA expression, analyzed by quantitative real-time RT-PCR at 0.5, 1, 2, 4, and 6 hours after the addition of PBS (mock-treated) or M-CSF+IL-4 combination, in the monocytes sorted by CD14 antibody-conjugated magnetic beads. The Col II mRNA expression was normalized to the house-keep gene expression of glyceraldehyde 3-phosphate (GAPDH) and shown as the fold difference at the indicated times. The CD14$^+$ monocytes are sorted from the PBMNCs before (Panel C and D) or after (Panel A and B) the M-CSF+IL-4 treatment.

FIG. 10 is an assembly of photos showing the therapeutic effect of one embodiment of the modified macrophages of the present invention on arthritic joints. The left panel A shows the hind knee joints of a rat without arthritis, treated with modified macrophages (cells) or without modified macrophages (PBS). The right panel A shows hind knee joints of rats with adjuvant (complete Freud's adjuvant, CFA)-induced arthritis, treated with modified macrophages (cell) or without modified macrophages (PBS). Panels B and C are line graphs illustrating thickness of knee swelling in rats with OA (panel C) or without OA (panel B), treated with the modified macrophages of the present invention.

FIG. 11 is a line graph illustrating the effect of modified macrophages of the present invention on the Knee injury and Osteoarthritis Outcome Score (KOOS) from treated patients. ADL stands for activity of daily life and QOL stands for knee-related quality of life.

FIG. 12 includes line graphs illustrating the paw diameter of C57BL/6 mice (Panel A and B) and Sprague-Dawley rats (Panel C and D) with collagen-induced rheumatoid arthritis, treated with (Panel B and D) or not treated with (Panel A and C) the modified macrophages of the present invention.

FIG. 13 shows the modified macrophages of the present invention significantly increased the range of movement in traumatic arthritis.

FIG. 14 is an assembly of fluorescent immunocytochem-istry staining images showing the formation of a cartilage-like membrane or structure over the cartilage surface of a joint cavity (Panel A) and within the bone (Panel B), 2 months after administering the modified macrophages in immune-deficient mice. Panel C shows background signal of the bone without injecting the modified macrophage of the present invention in immune-deficient mice.

FIG. 15 is an assembly of bar graphs illustrating the effect of M-CSF on mRNA gene expression of CD206 (panel A), gene expressions of anti-oxidant scavengers, such as HMOX1 (heme oxygenase 1) and FDX1L (ferredoxin 1-like, FDX2) (panel B), and gene expressions of collagen V (Collagen V alpha 1, Col5A1), procollagen C-endopep-tidase enhancer 2 (PCOLCE2) and heparan sulfate glu-cosamine 3-O-sulfotransferase 1 (HS3ST1) (Pane C) in modified macrophages.

DETAILED DESCRIPTION OF THE INVENTION

As used herein, the articles "a" and "an" refer to one or more than one (i.e., at least one) of the grammatical object of the article. By way of example, "a modified macrophage" means one modified macrophage or more than one modified macrophage.

An "effective amount," as used herein, refers to a dose of the modified macrophages or the pharmaceutical composi-tion disclosed herein that is sufficient to result in formation of cartilage or improvement in one or more symptoms and signs of musculoskeletal disease, which include, but are not limited to, pain, joint swelling and stiffness, which is detectable, either clinically as limited range of movement of a joint or radiologically through various imaging means.

The term "treating," "treated," or "treatment" as used herein refers to palliative uses or results, and/or slowing or inhibiting the advancement of musculoskeletal disease or the formation of cartilage.

The term "subject" can refer to a vertebrate suspected of having a musculoskeletal disease or to a vertebrate deemed to be in need of treatment for a musculoskeletal disease. Subjects include warm-blooded animals, such as mammals, a primate, and, more preferably, a human. Non-human primates are subjects as well. The term subject includes domesticated animals, such as cats, dogs, etc., livestock (for example, cattle, horses, pigs, sheep, goats, etc.) and laboratory animals (for example, mouse, rabbit, rat, gerbil, guinea pig, etc.). Thus, veterinary uses and medical formulations are contemplated herein.

The expression level or surface density of a surface marker, such as CD206, on the surface of the modified macrophages are "+" as long as the expression of the surface marker is detectable by conventional means. In one exemplary embodiment, "+" means that the cellular surface marker is detectably present in fluorescence activated cell sorting or magnetic beads over an isotype control; or is detectable above background in quantitative or semi-quantitative RT-PCR.

The terms "modified macrophages" and "polarized M2 macrophages" are used interchangeably.

As used herein, "substantially free" means that a composition contains less than 5%, 4%, 3%, 2% 1% or 0.5% of a specific substance, for example, a specific cytokine. In some embodiments, the composition does not contain the specific substance.

All numbers herein may be understood as modified by "about." As used herein, the term "about" is meant to encompass variations of ±10%.

Modified Monocytes and Macrophages

Modified monocytes of the present invention are derived from PBMNCs in the presence of a cell culture medium and a polarization mixture comprising macrophage-colony stimulating factor (M-CSF), granulocyte macrophage-colony stimulating factor (GM-CSF), granulocyte-colony stimulating factor (G-CSF), IL-4 or the combination thereof for about 1 hour to about 12 hours, lead to the polarization of modified monocytes. In one embodiment, the modified monocytes express surface marker CD14. In another embodiment, the modified monocytes carry a phenotype of CD14 (i.e., CD14$^+$) and express type II collagen (Col II) at protein or RNA level, resulting from the culturing methods of the present invention. In another embodiment, the contact time of the PBMNCs and the cell culture medium and a polarization mixture is about 1 hour to about 4 hours.

Modified macrophages of the present invention are derived from PBMNCs in the presence of a cell culture medium and a polarization mixture comprising M-CSF, GM-CSF, G-CSF, IL-4 or the combination thereof for about 12 hours to about 7 days, lead to the polarization of M2 macrophages. In one embodiment, the contact time of the PBMNCs and the cell culture medium and a polarization mixture is about 4 hours to about 7 days.

As shown in Table 1, Panel B of FIG. 4, the phenotypic characteristic of the so-called polarized M2 macrophages or modified macrophages is CD14$^+$CD206$^+$. In one embodiment, the modified macrophages express surface marker CD14. In another embodiment, the modified macrophages express surface marker CD206. In yet another embodiment, the modified macrophages express surface markers CD14 and CD206.

In one embodiment, the modified macrophages carry a phenotype of CD14 and CD206 (i.e., CD14$^+$CD206$^+$) and express type II collagen (Col II) at protein or RNA level, resulting from the culturing methods of the present invention.

TABLE 1

| Phenotypic characteristics of modified monocytes & modified macrophages | | | |
| --- | --- | --- | --- |
| | CD14 | mannose receptor C type 1 (MRC1, CD206) | Col II |
| modified monocytes | + | -- | + |
| modified macrophages | + | + | + |

The modified monocytes or modified macrophages of the present invention are non-naturally occurring. The modified monocytes or modified macrophages possess Col II in the cytoplasm, or on the cytoplasmic membranes of the modified monocytes or modified macrophages. In one embodiment, the modified macrophages of the present invention enhance the conversion of M1 macrophages to M2 macrophages, suppress the function of M1 macrophages, reduce chondrocyte apoptosis, decrease cartilage lesions, and increase cartilage formation.

The modified macrophages can be from a single individual, i.e., autologous, or pooled from multiple individuals (non-autologous allogeneic).

In one embodiment, the present invention provides pharmaceutical compositions comprising at least one modified monocyte or modified macrophage described herein, and a pharmaceutically acceptable vehicle, carrier or excipient. In some embodiments, the pharmaceutical composition comprises about 0.01% to 99.9% of modified macrophage or modified monocyte and about 0.1 to 99.99% of a pharmaceutically acceptable carrier or excipient. In some embodiments, the pharmaceutical composition comprises about 1% to 90% of modified macrophage or modified monocyte and about 10% to 99% of a pharmaceutically acceptable carrier or excipient.

Suitable vehicles are, for example, water, saline, dextrose, glycerol, ethanol, or the like, and combinations thereof. Suitable excipients are, for example, wetting agent, emulsifying agents or pH buffering agents. Pharmaceutically acceptable carriers can contain a physiologically acceptable compound that acts to, e.g., stabilize, or increase or decrease the absorption or clearance rates of the pharmaceutical compositions of the invention. Physiologically acceptable compounds can include, e.g., carbohydrates, such as glucose, sucrose, or dextrans, antioxidants, such as ascorbic acid or glutathione, chelating agents, low molecular weight proteins, detergents, liposomal carriers, or other stabilizers and/or buffers. Other physiologically acceptable compounds include wetting agents, emulsifying agents, dispersing agents or preservatives. The excipients may be nonionic surfactants, polyvinylpyrollidone, human serum albumin, aluminum hydroxide, agents with anesthetic action, and various unmodified and derivatized cyclodextrins. In one embodiment, the nonionic surfactants may include Polysorbate 20, Polysorbate 40, Polysorbate 60, and Polysorbate 80. The polyvinylpyrollidone may preferably be Plasdone C15, a pharmaceutical grade of polyvinylpyrollidone. The pharmaceutical composition comprising such excipient or carrier are formulated by well-known conventional methods.

In an exemplary embodiment, the pharmaceutical composition is substantially free of bone marrow-derived mesenchymal stromal cells.

The invention also provides methods of inhibiting musculoskeletal disease by administering to a subject in need thereof the modified macrophages, the modified monocyte or the pharmaceutical composition described herein in an amount effective to reduce the symptoms or signs of the musculoskeletal disease. The invention further provides methods of cartilage formation in a body site of a subject, by administering to the subject in need thereof the modified macrophages, the modified monocytes or the pharmaceutical composition of the present invention in an effective amount to form cartilage. Without being bound by any particular theory, it is believed that the modified macrophages or modified monocytes reduce the symptoms or signs of the musculoskeletal disease by one or more of the following mechanisms: enhance the conversion of M1 macrophages to M2 macrophages, suppress the function of M1 macrophages, reduce chondrocyte apoptosis, decrease cartilage lesions and increase cartilage formation. Given many of the musculoskeletal muscle diseases, such as OA and rheumatoid arthritis (RA), are characterized by progressive degeneration of the articular cartilage and leading to symptoms such as increasing pain, locking and giveaway, the formation of cartilage in the affected joint or sites greatly reduces the symptoms and signs caused by the degeneration of cartilage.

In a further embodiment of the present invention there is provided the use of the modified monocytes or modified macrophages as described herein for the manufacture of a medicament for the treatment of musculoskeletal disease.

Non limiting examples of the musculoskeletal disease including arthritis such as autoimmune arthritis, osteoarthritis (OA), and traumatic arthritis, degenerative disc disease, or conditions that affect the muscle, tendon or ligament, such as muscle sprain, and tendinitis.

Non limiting examples of autoimmune arthritis including RA, psoriatic arthritis and ankylosing spondylitis. Non limiting examples of degenerative disc disease is intervertebral disc degeneration.

Routes of administration of the present pharmaceutical compositions, modified monocytes or modified macrophages include, but are not limited to, intravenous, intramuscular, subcutaneous, oral, topical, subcutaneous, intradermal, transdermal, subdermal, parenteral, rectal, spinal, intrathecal, intraventricular, intraarticular or intervertebrate administration. In one embodiment, the modified macrophages are administered by intravenous injection or infusion.

The modified monocytes or modified macrophages of the present invention can also be administered with one or more therapeutic agents for treating musculoskeletal diseases. Non limiting examples of therapeutic agents for treating musculoskeletal diseases include hyaluronic acid or a derivative or salt thereof, growth factor, chondrogenic agent, vitamin D3 (cholecalciferol), collagen hydrolyzate, rusalatide acetate, avocado soy unsaponifiables (ASU), a steroid, a non-steroidal anti-inflammatory agent (NSAID) or the combination thereof. The modified macrophages can be administered simultaneously, before or after the therapeutic agents for treating musculoskeletal diseases.

The modified monocytes or modified macrophages of the present invention are formulated into pharmaceutical compositions for delivery to a mammalian subject. The pharmaceutical composition is administered alone, and/or mixed with a pharmaceutically acceptable vehicle, excipient or carrier. The vehicle, excipient or carrier is selected so as not to affect the biological activity of the combination. Suitable vehicles are, for example, saline, dextrose, glycerol, or the like, and combinations thereof. In addition, the vehicle can contain minor amounts of auxiliary substances such as wetting or emulsifying agents, pH buffering agents, or adjuvants. Pharmaceutically acceptable carriers can contain a physiologically acceptable compound that acts to, e.g., stabilize, or increase or decrease the absorption or clearance rates of the pharmaceutical compositions of the invention. Physiologically acceptable compounds can include, e.g., carbohydrates, such as glucose, sucrose, or dextran, antioxidants, such as ascorbic acid or glutathione, chelating agents, low molecular weight proteins, detergents, liposomal carriers, or excipients or other stabilizers and/or buffers. Other physiologically acceptable compounds include wetting agents, emulsifying agents, dispersing agents or preservatives. See e.g., the 21st edition of Remington's Pharmaceutical Science, Mack Publishing Company, Easton, Pa. ("Remington's"). The pharmaceutical compositions of the present invention can also include ancillary substances, such as pharmacological agents, cytokines, or other biological response modifiers.

Actual methods of preparing such dosage forms are known, or will be apparent, to those skilled in the art. See, e.g., Remington's Pharmaceutical Sciences, Mack Publishing Company, Easton, Pa., 21st edition.

The modified monocytes, modified macrophages or the present pharmaceutical compositions can be administered in a single dose treatment or in multiple-dose treatments on a schedule and over a time period appropriate to the age, weight and condition of the subject, the particular composition used, and the route of administration, whether the modified macrophages or the present pharmaceutical composition is used for prophylactic or curative purposes, etc. In some embodiments, the modified monocytes, modified macrophages or the present pharmaceutical composition is administered once a year, once every 6 months, once every 4 months, once every 3 months, once per month, twice per month, three times per month, once every other week (qow), once per week (qw), twice per week (biw), three times per week (tiw), four times per week, five times per week, six times per week, every other day (qod), daily (qd), twice a day (qid), or three times a day (tid).

The data obtained from the cell culture assays and animal studies can be used in formulating a range of dosages for use in humans. In one embodiment, the dosage of such modified macrophages lies within a range of circulating concentrations that include the $ED_{50}$ with little or no toxicity. The dosage can vary within this range depending upon the dosage form employed and the route of administration utilized. In another embodiment, the therapeutically effective dose can be estimated initially from cell culture assays. A dose can be formulated in animal models to achieve a circulating plasma concentration range that includes the $IC_{50}$ (i.e., the concentration of the modified macrophages which achieves a half-maximal inhibition of symptoms) as determined in cell culture. Sonderstrup, Springer, Sem. Immunopathol. 25: 35-45, 2003. Nikula et al., Inhal. Toxicol. 4(12): 123-53, 2000.

The pharmaceutical composition is formulated to contain an effective amount of the modified monocytes or modified macrophages described herein, wherein the amount depends on the subject to be treated and the condition to be treated. The specific dose level for any particular subject depends upon a variety of factors including the activity of the specifically modified monocytes or modified macrophages, the age, body weight, general health, sex, diet, time of administration, route of administration, and rate of excretion, drug combination and the severity of the particular disease undergoing therapy. An exemplary, non-limiting range for a therapeutically or prophylactically effective amount of the modified monocytes or modified macrophages of the present invention is at least about $1\times10^4$ cells per dose to about $1\times10^{10}$ per dose. Other dosages are also possible, including, but not limited to, $1\times10^5$, $1\times10^6$, $1\times10^7$, $2\times10^7$, $1\times10^8$ or $1\times10^9$.

The modified monocytes, modified macrophages or the pharmaceutical composition can be administered alone or in combination with at least one of the following agents or any agent for treating musculoskeletal disease: hyaluronic acid or a derivative or salt thereof, growth factor, chondrogenic agent, vitamin D3 (cholecalciferol), collagen hydrolyzate, rusalatide acetate, avocado soy unsaponifiables (ASU), a steroid and a non-steroidal anti-inflammatory agent (NSAID).

In Vitro Culture Methods for Producing Modified Macrophages

In one embodiment, the in vitro culture method to generate modified macrophages comprises the following phases:

(a) Collecting a sample from a subject. The sample includes, but is not limited to, any body fluid containing one or more mononuclear cells, such as peripheral blood, cord blood or bone marrow sample.

(b) Separating the modified macrophage in the sample of step (a) from other types of blood cells using the density-gradient centrifugation technique (e.g., Ficoll-Paque™ PREMIUM, GE Healthcare USA). Other methods of separating mononuclear cells are known, or will be apparent, to those skilled in the art.

(c) Methods of determining the % of monocytes are known in the art, by labeling the mononuclear cells in step (b) with antibodies to CD14 (e.g., anti-CD14 FITC conjugated antibody, commercially available from BioLegend, USA) and using flow cytometry.

(d) Methods for contacting purified modified macrophage with a cell culture medium and a polarization mixture comprising M-CSF, GM-CSF, G-CSF, IL-4 or a combination thereof.

In an exemplary embodiment, the polarization mixture is substantially free of IL-10, IL-13 or TGF-β. In another exemplary embodiment, the polarization mixture comprises about 40-60 weight % of M-CSF and about 40-60 weight % of IL-4 or about 50 weight % of M-CSF and about 50 weight % of IL-4.

An exemplary non-limiting range for the contact time of the PBMNCs and the polarization mixture for the formation of modified macrophages is from about 4 hours to about 12 hours, from about 1 day to about 3 days, from about 2 days to about 5 days, from about 1 day to about 6 days, from about 1 day to about 7 days, from about 1 day to about 8 days, from about 1 day to about 9 days, from about 1 day to about 10 days, at least 1 day, at least 2 days, at least 3 days, at least 4 days, at least 5 days, at least 6 days or at least 7 days. In one embodiment, the contact time is about 4 hours to 24 hours. In one embodiment, the contact time is about 4 hours to about 7 days.

The term "cell culture medium" refers to any medium suitable for the culture of mammalian cells. Media may be solid, liquid, gaseous or a mixture of phases and materials. Media include liquid growth media, gelatinous media such as agar, agarose, gelatin and collagen matrices. Exemplary gaseous media include the gaseous phase that cells growing on a petri dish or other solid or semisolid support are exposed to. Non limiting examples of cell culture medium include RPMI-1640 or Iscove's Modified Dulbecco's Medium (IMDM).

The following examples of specific aspects for carrying out the present invention are offered for illustrative purposes only, and are not intended to limit the scope of the present invention in any way.

EXAMPLES

Example 1: The Isolation of Peripheral Mononuclear Cells (PBMNCs)

A peripheral blood sample was collected from a donor and stored in a collecting tube with EDTA. One hundred mL of the peripheral blood sample was carefully loaded on the interface of 100 mL Ficoll-Paque premium. After centrifuging at 700×g for 15 min, the cells in the upper layer of the tube (i.e., PBMNCs) and were transferred to 50 mL tubes. The cell pellet was obtained after centrifuging at 500×g for 5 min and the % of monocyte in the cell pellet was measured by flow cytometry using anti-CD14 FITC conjugated antibody (BioLegend, USA). In general, $0.8\text{-}1.5\times10^8$ PBMNCs can be harvested from 100 mL blood.

Example 2: The Activation and Polarization of the PBMNCs into Modified Macrophages The PBMNCs (including lymphocytes, monocytes and NK cells) obtained in Example 1 were incubated with (a) RPMI-1640 (#31800, Gibco)+human platelet lysate (Compass) (control), (b) 100 ng/mL M-CSF (#216-GMP-500, R&D SYSTEMS), (c) 100 ng/mL GM-CSF (#300-03, PEPROTECH) or (d) 100 ng/mL G-CSF (#300-23, PEPRO-TECH) for 3 days on 2.5 µg/cm² fibronectin (#07159, STEMCELL Technologies)-coated slides. Amongst the cultured PBMNCs, monocyte-derived macrophages could adhere to the slides and were incubated with a fixation buffer (#420801, BioLegend), permeabilized with an intracellular staining permeabilization wash buffer (#421002, BioLegend) and stained with an anti-Col II antibody (#AB761, Millipore) for 1 hour. Col II expressing cells were visualized with green Alexa Fluor 488 goat anti-rabbit IgG antibody (#A11008, Invitrogen). The total cell number was estimated by the DAPI staining in the nuclei (blue). FIG. 1 show the % of Col II expressed in PBMNCs cultured with M-CSF (i.e., cultured monocyte-derived macrophages) is about 55%, about 40% in PBMNCs cultured with GM-CSF (i.e., cultured monocyte-derived macrophages) and about 25% in PBMNCs cultured with G-CSF (i.e., cultured monocyte-derived macrophages).

Col II expression in monocyte-derived macrophages (isolated from PBMNCs cultured with M-CSF) was further verified by fluorescent immunocytochemistry staining using monoclonal (#MA5-12789, Invitrogen) and polyclonal (#AB761, Millipore). FIG. 2 shows Col II expressed both in the cytosol and on cytoplasmic membrane of the cultured monocyte-derived macrophages.

The PBMNCs were purified from peripheral blood using Ficoll-Paque and subjected to flow analysis. The monocyte population was identified by the distribution in the plot of forward scatter (FSC) and side scatter (SSC) and the expression of CD14 surface antigen. The flow analysis result shows that the peripheral blood sample included 18.6% of monocytes according to the FSC/SSC plot and 18.8% monocytes using surface immunostaining of CD14 (FIG. 3, panel A). This result indicates that either gating strategy using FSC/SSC or immunostaining can faithfully verify the cell population of monocyte/macrophage.

The PBMNCs were cultured with (a) RPMI-1640+human platelet lysate (control), (b) 100 ng/mL M-CSF, (c) 100 ng/mL GM-CSF or (d) 100 ng/mL G-CSF in low-binding dishes to maintain the cell suspension status. After 3 days culture, the living suspended cells were stained with anti-Col II antibody for 1 hour to detect the expression of Col II on cytoplasmic membrane. Panel B and panel C of FIG. 3 show that the % of Col II expression is about 15% by M-CSF, about 8% by GM-CSF and about 6.5% by G-CSF in the treated monocytes (FSC/SSC gated cells in panel A).

The cultured PBMNCs were co-stained with anti-CD14 and anti-Col II antibodies on day 3 and day 7 (Panel A of FIG. 4) to identity the cells expressing Col II. Most of the cultured PBMNCs have transformed to CD14$^+$ monocytes and the expression of Col II was in a time dependent manner. With the treatment of 100 ng/mL M-CSF for 4 hours or more, CD14$^+$ monocytes were polarized to become CD14$^+$ CD206$^+$ M2 macrophage (Panel B of FIG. 4). Panel C of FIG. 4 further reveals that a unique subgroup in M2 macrophage population, named modified macrophage in this invention, which expressed Col II, CD14 and CD206 proteins on day 5.

To further confirm the cell identity of Col II-expressing cells, the treated PBMNCs with M-CSF, GM-CSF or G-CSF were double stained with anti-CD206 antibody (#555954, BD Pharmingen™, red), a specific M2 macrophage marker, and anti-Col II antibody (green) for 1 hour. The total cell number was analyzed by DAPI-stained nuclei. Panels A of FIG. 5 reveals a unique subgroup in M2 macrophage population, the modified macrophage in the present invention, which expresses both Col II and CD206 proteins. Panel B of the FIG. 5 shows that the ratio of modified macrophage (col II/CD206, double-positive cells) in the cultured PBMNCs was significantly induced by M-CSF, GM-CSF and moderately induced by G-CSF after 3 days of culture.

Example 3: The Effect of Various Cytokines on Col II Expression

The PBMNCs from Example 2 were isolated and cultured with (a) RPMI-1640+human platelet lysate (negative control), (b) 100 ng/mL interleukin-4 (IL-4, #204-GMP-01M), (c) 20 ng/mL interleukin-10 (IL-10, #200-10, PEPRO-TECH), (d) 20 ng/mL interleukin-13 (IL-13, #200-13, PEPROTECH), (e) 20 ng/mL transforming growth factor beta (TGF-β, #100-21, PEPROTECH) for 1 day. Cultured cells were stained with anti-CD206 and anti-Col II antibody for 1 hour. Cell populations were first gated based on the FSC/SSC and immunostaining to identify modified macrophage population based on Col II and CD206 expression.

Panels A and B of FIG. 6 show IL-4 induced the highest ratio of modified macrophage with Col II/CD206 double expression in total PBMNCs population among the tested cytokines.

Example 4: The Effect of Various Dosages of M-CSF or GM-CSF on Col II Expression The PBMNCs of Example 2 were treated with 2, 10, 20, 50 and 100 ng/mL (A) M-CSF or (B) GM-CSF for 3 days. Cells were stained with an anti-Col II antibody for 1 hour. Gating strategy was used in flow cytometry analysis. Cell populations were first gated based on the FSC-A and SSC-A to identify monocytes, and monocytes were further analyzed based on Col II expression.

FIG. 7 show that M-CSF or GM-CSF activates Col II expression in a dose-dependent manner.

Example 5: The Synergistic Effect of M-CSF/IL-4 Combination and GM-CSF/IL-4 Combination on Col II Expression The PBMNCs from Example 2 were cultured with (a) RPMI-1640+human platelet lysate (control), (b) 100 ng/mL IL-4, (c) 100 ng/mL M-CSF, (d) 100 ng/mL M-CSF+100 ng/mL IL-4, for 3 days on 2.5 ug/cm$^2$ fibronectin-coated slides.

Another population of PBMNCs from Example 2 were cultured with (a) RPMI1640+human platelet lysate (control), (b) 100 ng/mL IL-4, (c) 100 ng/mL GM-CSF, (d) 100 ng/mL GM-CSF+100 ng/mL IL-4, for 3 days on 2.5 ug/cm$^2$ fibronectin-coated slides.

The cultured PBMNCs were fixed with a fixation buffer, permeabilized with an intracellular staining permeabilization wash buffer and stained with an anti-CD206 antibody on the cytoplasmic membrane and anti-collagen type II antibody in the cytosol for 1 hour. Cells were visualized with the staining of Alexa Fluor 488 goat anti-rabbit IgG antibody. The total cell number was analyzed by DAPI-stained nuclei.

Panel A of FIG. 8 shows the synergistic effect of M-CSF/IL-4 combination on modified macrophages (Col II/CD206 double-positive cells) induction from the cultured PBMNCs. Panel B of FIG. 8 shows the synergistic effect of GM-CSF/IL-4 combination on modified macrophages induction.

Example 6: The Effect of Incubation Time on Col II Expression of Modified Monocytes The PBMNCs from Example 2 were cultured with (a) phosphate buffer saline or PBS (mock-treated) or M-CSF (100 ng/mL) and IL-4 (100 ng/mL) combination at 0.5, 1, 2, 4, and 6 hours. The monocytes amongst the cultured PBMNCs were sorted with anti-CD14 antibody on magnetic beads and then the total RNAs were extracted and the expression levels were analyzed by real-time reverse transcriptase-polymerase chain reaction (RT-PCR). The RNA expression level of Col II was normalized to that of glyceraldehyde 3-phosphate (GAPDH) and the fold differences were compared to PBS controls.

Panels A to D of FIG. 9 show the M-CSF/IL-4 combination affects Col II expression in CD14 monocytes in a time-dependent manner. At 2 hours induction, the Col II mRNA expression was about 2 fold induction and show significant higher than that of control (p<0.001, ***). The CD14$^+$ monocytes were sorted from the PBMNCs before (Panel C and D) or after (Panel A and B) the M-CSF+IL-4 treatment. CD14$^+$ monocytes obtained from PBMNCs before or after the cytokines treatment showed similar Col II expression patterns, demonstrating that the polarization factors directly activated the monocytes toward Col II-expressing cells, rather than through an indirect pathway from non-monocytes population in PBMNCs.

Example 7: In Vivo Evaluation of the Effect of Modified Macrophages in OA Rats Ten adult male Sprague-Dawley (SD) rats, weighing 200-210 g, were housed in a room with constant temperature (24-26° C.) and humidity (40-60%) and had free access to food and water.

The hind knee joint of each rat was injected with 0.25 mL of complete Freund's adjuvant (CFA, commercially available from Sigma, USA) to induce OA. On day 6, the inflammation was boosted by injecting another 0.05 mL of CFA into the same joint. On Day 7, when the arthritis was established, the arthritic knee joints were treated with 0.2 mL of PBS (control) or $2\times10^5$ M-CSF/IL-4-induced modified macrophages in 0.2 mL PBS. Non-binding cytokines to the cells were cleared by PBS wash twice. Knee joints were measured using a vernier every 2-3 days for two weeks.

Four adult male SD rats (healthy control) and 16 rats with CFA-induced arthritis were included in this study. Seven days after the arthritis induction, 8 rats were treated with 0.2 mL PBS (mock) and the other 8 rats were treated with the treated cells in 0.2 mL PBS. The diameter of each knee joint was measured every 2-3 days for 25 days post treatment. On Day 25, all of the rats treated with PBS showed a classical symptom of arthritis (joint swelling). Notably, the modified macrophages significantly reduced the progression and the severity of the arthritis and joint swelling (p<0.01) (FIG. 10). The inhibition of the arthritis could not be mediated by the polarization factors as the cells were washed to completely remove the original culture medium before modified macrophage injection. These results strongly suggest that the modified macrophages can be a therapeutically effective agent for controlling arthritis.

Example 8: Clinical Study to Evaluate the Effect of Modified Macrophages in OA A prospective clinical study was approved by the Research Ethics Committee of Chinese Medical University and Hospital in Taichung, Taiwan (CMUH109-Rec1-012) and carried out in Asia University Hospital, Taichung, Taiwan.

Patients with chronic osteoarthritis were included in this study and were excluded from the study if they have any one of the following: oncologic diseases, severe anemia, thrombocytopenia and infectious diseases. Five patients were enrolled in the study and informed consent was obtained from all of the enrolled patients.

The severity of OA was assessed using the Kellgren-Lawrence (K-L) grading system based on the X-ray. A single intra-articular injection of $1\times10^8$ autologous PBMNCs cultured with M-CSF for 5 days, containing $1$-$3\times10^7$ modified macrophages of the present invention, was administered by the principal investigator. Six months after the intra-articular injection, the progression of OA was evaluated by the Knee injury and Osteoarthritis Outcome Score (KOOS), a questionnaire designed to evaluate the knee and assesses given outcomes: pain, other symptoms, activities of daily living, sport and recreation function, and knee-related quality of life.

FIG. 11 shows the modified macrophages of the present invention significantly improved the pain, sports, and knee-related quality of life (p<0.05).

Example 9: In Vivo Evaluation of the Effect of Modified Macrophages in RA Rats Collagen-induced arthritis (CIA) in rodents is a classical model of human RA. CIA induced RA was successfully established in both C57BL/6 mice and Sprague-Dawley rats via the subcutaneous injection of type II collagen (200 µg) into the tail vein. Significant paw swelling was observed on day 40 and persisted to day 105. The $2\times10^5$ modified macrophage of the present invention was intra-articularly injected into the left knee of each mouse or rat on day 50 (1st dose) and day 80 ($2^{nd}$ dose) and the PBS (phosphate buffer saline) was intra-articularly injected into the right knee of each mouse or rate as a mock-treatment control. FIG. 12 show the modified macrophage of the present invention significantly reduced paw swelling in both RA-mice and RA-rats and the effect lasted at least 25 days after the $2^{nd}$ dose.

Example 10: Clinical Evaluation on the Effect of Modified Macrophages in Traumatic Arthritis A 45-year-old male patient suffered from traumatic arthritis in the proximal interphalangeal joint of his right middle finger as the result of phalangeal fracture. He continued to experience pain and was unable to flex the affected joint (arrow on the left, FIG. 13).

The patient was given the $1.5\times10^8$ autologous PBMNCs cultured in M-CSF for 5 days, containing $3.5\times10^7$ modified macrophage of the present invention, into the affected joint by intra-articular injection about 4 months after the injury. The joint pain improved significantly one week after the injection and 3 weeks after the treatment, he was able to fully flex the affected joint (arrow on the right, FIG. 13).

Example 11: Formation of Cartilage Over the Joint Surface and within the Bone The modified macrophages ($2\times10^5$ cells) of the present invention were administered into the joint cavity and the bones of immune-deficient mice. Immunochemical staining of the joint cavity and bone at 2-month post injection showed the formation of cartilage-like membrane or a cartilage-like structure (human Col II stained as green in the cytoplasm and stained as blue with DAPI in the nuclei) over the cartilage surface in the joint cavity (Panel A) and within the bone (Panel B) in immune-deficient mice (FIG. 14). Panel C of FIG. 14 shows the background signal of the corresponding bone/joint cavity not injected with the modified macrophages of the present invention.

Example 12: The Effect of M-CSF on CD206, Anti-Oxidant Scavengers & Bone Constitute Formation The PBMNCs were cultured with M-CSF at the following concentrations for 24 hours: 0, 2, 10, 50 and 100 ng/mL. The modified macrophages, sorted by the magnetic beads with anti-CD14 Antibody as Example 6, were subjected to the extraction of total RNA using Trizol and chloroform solutions, following the standard RNA isolation protocol of Phalanx Biotech Company (Taiwan). The RNA samples were examined by OD260, OD280, OD230, agarose electrophoresis, RNA quality and quantity (Agilent Bioanalyzer, Agilent RNA 6000 Nano/Pico Assay). The quality of purity and integrity were validated and passed by the Phalanx Biotech Company (Taiwan).

Fluorescent antisense RNA (CyDye-aRNA) targets were prepared from 1 µg RNA samples and synthesized by adding aminoallyl-uridine-5'-triphosphate and NHS-CyeDye using OneArray (Registered Trademark) Amino Allyl aRNA Amplification kit (Phalanx Biotech, Taiwan). Fluorescent cDNA samples were hybridized to the Human Whole Genome OneArray (Registered Trademark) and processed following the routine protocol of Phalanx Biotech Company. The fluorescent signals were scanned by Agilent Microarray Scanner (G2505C) and the intensities of each probe were obtained by GenePix 4.0 software (Molecular Devices, USA).

The raw intensity of the chips was analyzed Rosetta Resolver System (Registered Trademark) 7.0 (Rosetta Biosoftware; Merck, USA) to process the data analysis. The intensity of the probes that passed the criteria were normalized by a 50% median scaling normalization method. The repeated data were validated by Pearson correlation coefficient calculation to confirm the reproducibility (R value>0.975). Normalized spot intensities were shown as gene expression $\log_2$ ratios between the control and treatment groups. The probes with $\log_2$ ratio$\geq$1 or $\log_2$ ratio$\leq$−1 and p<0.05 were selected as differential expressed genes for further signal pathway analysis.

Panel A of FIG. 15 shows gene expression of CD206 (also named as mannose receptor C-type 1, MRC1) in the modified macrophages is between 4 to 6 folds regardless of the M-CSF concentration. Panel B of FIG. 15 shows M-CSF increases the gene expression of anti-oxidant scavengers, HMOX1 (heme oxygenase 1) and FDX1L (ferredoxin 1-like, FDX2) in the modified macrophages in a dose-dependent manner. Panel C of FIG. 15 shows M-CSF enhances the expression of bone constitute formation genes in the modified macrophages, such as collagen V (Collagen V alpha 1, Col5A1), procollagen C-endopeptidase enhancer 2 (PCOLCE2) and heparan sulfate glucosamine 3-O-sulfotransferase 1 (HS3ST1). Collagen V is a main constitute of the bone-muscular tissues and PCOLCE2 is essential for the maturation of collagen and the deposition of fibrillary collagen. HS3ST1 is a rate-limiting enzyme for the synthesis of heparan sulfate, an important component for bone, cartilage and tendon formation.

The invention claimed is:

1. A macrophage, comprising
a macrophage phenotype CD14$^+$CD206$^+$; and
type II collagen expression.

2. The macrophage of claim 1, wherein the type II collagen is expressed within the macrophage.

3. The macrophage of claim 1, wherein the type II collagen is expressed on the surface of the macrophage.

4. A monocyte, comprising
a monocyte phenotype CD14$^+$; and
type II collagen expression.

5. The monocyte of claim 4, wherein the type II collagen is expressed within the monocyte.

6. A pharmaceutical composition, comprising
(a) the macrophage of claim 1; and
(b) a pharmaceutically acceptable carrier or excipient.

7. The pharmaceutical composition of claim 6, comprising about 0.01% to 99.9% of the macrophage.

8. A method of treating a musculoskeletal disease, comprising administering an effective amount of the macrophage of claim 1 to a subject in need thereof to treat the musculoskeletal disease.

9. The method of claim 8, wherein the musculoskeletal disease is arthritis.

10. The method of claim 9, wherein the arthritis is osteoarthritis, autoimmune arthritis or traumatic arthritis.

11. The method of claim 8, wherein the musculoskeletal disease is degenerative disc disease or intervertebral disc degeneration.

12. The method of claim 11, wherein the disc is selected from the group consisting of the cartilage tissue portion of articulate cartilage, the cartilage tissue portion of a meniscus and the cartilage tissue portion of an intervertebral disc.

13. The method of claim 8, wherein the musculoskeletal disease is tendinitis.

14. The method of claim 8, wherein the macrophage is administered by intra-articular injection.

15. The method of claim 8, further comprising administering to the subject an agent selected from hyaluronic acid or a derivative or salt thereof, growth factor, chondrogenic agent, vitamin D3 (cholecalciferol), collagen hydrolyzate, rusalatide acetate, avocado soy unsaponifiables (ASU), a steroid and a non-steroidal anti-inflammatory agent (NSAID).

16. A method of treating a musculoskeletal disease, comprising administering an effective amount of the monocytes of claim 4 to a subject in need thereof to treat the musculoskeletal disease.

17. A method of inducing cartilage formation in a body site of a subject, comprising administering an effective amount of the monocytes of claim 4 to a subject in need thereof to treat the musculoskeletal disease.

* * * * *